US012618071B2

(12) United States Patent
Brown

(10) Patent No.: US 12,618,071 B2
(45) Date of Patent: May 5, 2026

(54) MULTIMERIC OLIGONUCLEOTIDES WITH DIVIDED STRANDS

(71) Applicant: MPEG LA, L.L.C., Chevy Chase, MD (US)

(72) Inventor: Jonathan Miles Brown, Silver Spring, MD (US)

(73) Assignee: MPEG LA, L.L.C., Chevy Chase, MD (US)

( * ) Notice: Subject to any disclaimer, the term of this patent is extended or adjusted under 35 U.S.C. 154(b) by 0 days.

(21) Appl. No.: 17/985,005

(22) Filed: Nov. 10, 2022

(65) Prior Publication Data

US 2023/0146956 A1 May 11, 2023

Related U.S. Application Data

(63) Continuation of application No. 17/922,254, filed as application No. PCT/US2021/029984 on Apr. 29, 2021.

(60) Provisional application No. 63/018,406, filed on Apr. 30, 2020.

(51) Int. Cl.
*C12N 15/113* (2010.01)

(52) U.S. Cl.
CPC ........ *C12N 15/1137* (2013.01); *C12N 15/113* (2013.01); *C12N 2310/14* (2013.01); *C12N 2310/314* (2013.01); *C12N 2310/321* (2013.01); *C12N 2310/51* (2013.01); *C12N 2330/30* (2013.01)

(58) Field of Classification Search
CPC . C12N 15/1137; C12N 15/111; C12N 15/113; C12N 2310/14; C12N 2310/51; C12N 2310/3519; A61K 31/713
USPC ..................... 435/6.1, 91.1, 91.31, 455, 458; 514/44 A; 536/23.1, 24.5
See application file for complete search history.

(56) References Cited

U.S. PATENT DOCUMENTS 5,552,535 A 9/1996 McLean et al.
8,106,173 B2 1/2012 Kandimalla et al.
8,110,674 B2 2/2012 Manoharan et al.
8,188,261 B2 5/2012 Kandimalla et al.
8,362,233 B2 1/2013 Kandimalla et al.
8,431,544 B1 4/2013 Agrawal et al.
8,580,946 B2 11/2013 Park et al.
8,759,310 B2 6/2014 Kandimalla et al.
9,243,050 B2 1/2016 Kandimalla et al.
9,255,269 B2 2/2016 Park et al.
9,616,085 B2 4/2017 Hong et al.
9,644,209 B2 5/2017 Park et al.
10,597,659 B2 3/2020 Park et al.
11,078,484 B2 8/2021 Brown et al.
11,352,629 B2 6/2022 Hadwiger et al.
11,767,531 B2 * 9/2023 Hadwiger ............ A61K 47/549 536/23.1
11,859,184 B2 1/2024 Park et al.
2004/0235773 A1 11/2004 Zhao et al.
2007/0287681 A1 12/2007 Jeong et al.
2008/0108801 A1 5/2008 Manoharan et al.
2008/0214436 A1 9/2008 Yu et al.
2008/0287383 A1 11/2008 Quay et al.
2008/0311040 A1 12/2008 Berry et al.
2009/0126038 A1 5/2009 Van De Craen et al.
2013/0330293 A1 12/2013 Long et al.
2014/0194610 A1 7/2014 Verdine et al.
2015/0197754 A9 7/2015 Park et al.
2015/0299695 A1 10/2015 Uhlmann et al.
2015/0315585 A1 11/2015 Uhlmann et al.
2016/0193354 A1 7/2016 Noe et al.
2016/0298124 A1 10/2016 Borodovsky et al.
2016/0347780 A1 12/2016 Wada et al.
2017/0189525 A1 7/2017 Brunskill et al.
2017/0204408 A9 7/2017 Lewis
2017/0349896 A1 12/2017 Albaek et al.
2018/0080028 A1 3/2018 Park et al.
2018/0312839 A1 11/2018 Bhat et al.
2019/0062743 A1 2/2019 Uhlmann et al.
2019/0085331 A1 3/2019 Hadwiger et al.
2020/0239892 A1 7/2020 Park et al.
2020/0308578 A1 10/2020 Woolf et al.
2021/0380979 A1 12/2021 Brown et al.
2023/0114023 A1 4/2023 Brown et al.
2023/0220388 A1 7/2023 Brown
(Continued)

FOREIGN PATENT DOCUMENTS

EP 2395085 A2 12/2011
JP 2009-502198 1/2009
(Continued)

OTHER PUBLICATIONS

U.S. Appl. No. 17/922,254 (Year: 2022).*
(Continued)

*Primary Examiner* — Jane J Zara
(74) *Attorney, Agent, or Firm* — KNOBBE, MARTENS, OLSON & BEAR, LLP

(57) ABSTRACT

The present disclosure relates to multimeric oligonucleotides comprising subunits, each of the subunits independently comprises a single-stranded or double-stranded oligonucleotide. Each of the subunits is joined to another subunit by a covalent linker, and at least one subunit comprises at least one partial single-stranded oligonucleotide. The present disclosure also relates to methods of synthesizing the multimeric oligonucleotides and the methods of using the multimeric oligonucleotides disclosed herein.

14 Claims, 12 Drawing Sheets

Specification includes a Sequence Listing.

(56) References Cited

U.S. PATENT DOCUMENTS

| | | | | |
|---|---|---|---|---|
| 2023/0279390 | A1 | 9/2023 | Brown | |
| 2023/0287406 | A1* | 9/2023 | Brown | A61K 31/713 |

FOREIGN PATENT DOCUMENTS

| | | | | | |
|---|---|---|---|---|---|
| JP | 2014-527819 | | 10/2014 | | |
| JP | 2015-529469 | | 10/2015 | | |
| JP | 2017-565893 | A | 7/2018 | | |
| JP | 2011-518784 | | 10/2019 | | |
| KR | 10-2010-0089796 | | 8/2010 | | |
| KR | 10-2011-0083919 | A | 7/2011 | | |
| WO | WO 2004/030634 | A2 | 4/2004 | | |
| WO | WO 2004/090108 | A2 | 10/2004 | | |
| WO | WO 2004/091515 | A2 | 10/2004 | | |
| WO | WO 2004/094345 | A2 | 11/2004 | | |
| WO | WO 2004/094595 | A2 | 11/2004 | | |
| WO | WO 2007/117686 | A2 | 10/2007 | | |
| WO | WO-2008109105 | A2 * | 9/2008 | C12N 15/111 | |
| WO | WO 2009/014887 | A2 | 1/2009 | | |
| WO | WO 2009/126933 | A2 | 10/2009 | | |
| WO | WO2010/021720 | A1 | 2/2010 | | |
| WO | WO 2011/031520 | A1 | 3/2011 | | |
| WO | WO 2011/109380 | A1 | 9/2011 | | |
| WO | WO 2011/132672 | | 10/2011 | | |
| WO | WO 2013/040429 | A1 | 3/2013 | | |
| WO | WO-2014043544 | A1 * | 3/2014 | C12N 15/111 | |
| WO | WO 2014/208973 | | 12/2014 | | |
| WO | WO 2019/105421 | A1 | 6/2019 | | |
| WO | WO 2021/222635 | A2 | 11/2021 | | |
| WO | WO 2021/236689 | A1 | 11/2021 | | |

OTHER PUBLICATIONS

U.S. Appl. No. 17/747,924 (Year: 2022).*
Dubiley et al (Nucleic Acids Res., vol. 25, No. 12, pp. 2259-2265 (1997)).*
Parinov et al (Nucleic Acids Res., vol. 24, No. 15 (1996).*
Bui et al (New J. Phys., vol. 19, Pub. No. 015006, pp. 1-10 (2017)) (Year: 2017).*
Bordoni et al (Nucleic Acids Res., vol. 30, No. 8e34, pp. 1-7 (2002)) (Year: 2002).*
Lee et al (Biomaterials, vol. 32, pp. 2359-2368 (2011)) (Year: 2011).*
Yoo et al (Chem. Commun., vol. 50, pp. 6765-6767 (2014)) (Year: 2014).*
Mok et al (Nature Materials, vol. 9, pp. 272-278 (2010) (Year: 2010).*
Roberts et al (Nature Rev., Drug Discovery, vol. 19, pp. 673-694 (2020)) (Year: 2020).*
Osborn et al (Nucleic Acid Therapeutics, vol. 28, No. 3, pp. 128-136 (2018)) (Year: 2018).*
Damase et al (Frontiers in Bioengineering and Biotechnology, vol. 9, Article 628137, pp. 1-24 (2021)) (Year: 2021).*
Bost et al (ACS Nano, vol. 15, pp. 13993-14021 (2021)) (Year: 2021).*
Bordoni et al., "Investigation of the multiple anchors approach in oligonucleotide microarray preparation using linear and stem-loop structured probes", Nucleic Acids Research, Apr. 15, 2002, vol. 30, No. 8, article e34; pp. 1-7.
Bui et al., "Design and analysis or linear cascade DNA hybridization chain reactions using DNA hairpins", New Journal or Physics, 2017, vol. 19, article 015006; pp. 1-10.
Choi et a, "Next-Generation in Situ Hybridization Chain Reaction: Higher Gain, Lower Cost, Greater Durability", ACS Nano, May 27, 2014, vol. 8, No. 5, pp. 4284-4294.
Dubiley et al., "Fractionation, phosphorylation and ligation on oligonucleotide microchips to enhance sequencing by hybridization", Nucleic Acids Research, Jun. 15, 1997, vol. 25, No. 12; pp. 2259-2265.
Parinov et al., "DNA sequencing by hybridization to microchip octa-and decanucleotides extended by stacked pentanucleotides", Nucleic Acids Research, 1996, vol. 24, No. 15, pp. 2998-3004.
International Search Report and Written Opinion for International Application No. PCT/US2021/029984, mailing date Nov. 10, 2021, in 16 pages.
Bolcato-Bellemin et al. (2007), "Sticky overhangs enhance siRNA-mediated gene silencing," Proc. Natl. Acad. Sci. USA, 104:41: 16050-16055.
Bonger, K. M., "Dimeric ligands for GPCRs involved in human reproduction: synthesis and biological evaluation" pp. 1-217, Dec. 19, 2008.
Brown, JM et al., Ligan Conjugated Multimeric siRNAs Enable Enhanced Uptake and Multiplexed Gene Silencing. Nucieic Acid Therapeutics, Sep. 26, 2019, vol. 29, No. 5, pp. 231-244; entire document. DOI: 10.1089/nat.2019.0782.
Cellamare et al., "Design, synthesis, and biological evaluation of glycine-based molecular tongs as inhibitors of AB1-40 aggregation in vitro", Bioorganic & Medicinal Chemistry, vol. 16, 2008, pp. 4810-4822.
Elbashir et al. (2001), "Duplexes of 21-nucleotide RNAs mediate RNA interference in cultured mammalian cells," Nature, 411: 494-498.
Gary et al. (2007), "Polymer-based siRNA delivery: Perspective on the fundamental and phenomenological distinctions from polymer-based DNA delivery," J. Controlled Release, 121: 64-73.
Hong et al., "Gene Silencing by siRNA Microhydrogels via Polymeric Nanoscale Condensation", Aug. 2011, JAGS, 133: 13914-13917.
Jeong, J.H., et al., siRNA conjugate delivery systems. Bioconjug Chem. Jan. 2009;20(1):5-14. doi: 10.1021/bc800278e.
Kang et al. "HER2 RNA Aptamerand Cell Penetrating Peptide-Mediated Delivery of Multimeric Antisense Strands of siRNAs for Gene Silencing: Multimeric antisense strands of siRNAS", bull. Korean chem. Soc., vol. 37, No. 9, Aug. 29, 2016, pp. 1440-1444, XPO55746857, ISSN: 1229-5949, DOI: 10.1002/bkcs.10886.
Kashihara et al., "Analysis of Renal Microcirculation and Permeability-Change with Bio-Imaging Techniques", KENBIKYO, 2011, vol. 46, No. 3, p. 181-187.
Kim, S.H., et al., Local and systemic delivery of VEGF siRNA using polyelectrolyte complex micelles for effective treatment of cancer. J Control Release. Jul. 14, 2008;129(2): 107-16. doi: 10.1016/j.jconrel.2008.03.008. Epub Mar. 14, 2008.
Kim, S.H., et al., LHRH receptor-mediated delivery of siRNA using polyelectrolyte complex micelles self-assembled rom siRNA-PEG-LHRH conjugate and PEI. Bioconjug Chem. Nov. 19, 2008; 19(11):2156-62. doi: 10.1021/bc800249n.
Kim et al. (2006) "PEG conjugated VEGF siRNA for anti-angiogenic gene therapy," Journal of Controlled Release, 116:123-129.
Lee et al., (2012) "Molecularly Self-Assembled Nucleic-Acid Nanoparticles for Targeted in Vivo siRNA Delivery," Nature Nanotechnology, 7(6):389-393.
Lee et al., (2012) "Small-Interfering RNA (siRNA)-Based Functional Micro-and Nanostructures for Efficient and Selective Gene Silencing," Accounts of Chemical Research, 45(7):1014-1025.
Mok et al., "Self-crosslinked and reducible fusogenic peptides for intracellular delivery of siRNA", Biopolymers. J008 Ocl;89(10):881-8. doi: 10.1002/bip.21032.
Moschos, S.A, et al., Lung delivery studies using siRNA conjugated to TAT(48-60) and penetralin reveal peptide nduced reduction in gene expression and induction of innate immunity. Bioconjug Chem. Sep.-Oct. 2007;18(5):1450-9. Epub Aug. 21, 2007.
Motoyashi et al., "Glomerular Disease and tubule injury", Japanese Journal of Pediatric Nephrology, 2009, vol. 22, No. 2, p. 76-81.
Muratovska, A., et al., Conjugate for efficient delivery of short interfering RNA (siRNA) into mammalian cells. FEBS Lett. Jan. 30, 2004;558(1-3):63-8.
Rinsho Yakuri, Japanese Journal of Clinical Pharmacology and Therapeutics, 2016, vol. 47, No. 2, p. 56-61.
Schiffelers RM, et al. "Cancer siRNA therapy by tumor selective delivery with ligand-targeted sterically stabilized nanoparticle", Nucleic Acids Res. 32 (2004) e149. Published Oct. 1, 2004.

(56) References Cited

OTHER PUBLICATIONS

Subramanian et al., “Enhancing Antisense Efficacy with Multimers and Multi-Targeting Oligonucleotides (MTOs) Using Cleavable Linkers,” Nucleic Acids Research, Oct. 7, 2015, vol. 43, Issue 19, pp. 9123-9132.
Sugo, T. et al., Development of antibody-siRNA conjugate targeted to cardiac and skeletal muscles, Journal of Controlled Release, 237 (2016) 1-13.
Sun et al., (1997) “Synthesis of 3'-thioribonucleosides and their incorporation into oligoribonucleotides via phosphoramidite chemistry,” RNA, 3(11 ):1352-63.
Tai, Wanyi, Bin Qin, and Kun Cheng. “Inhibition of breast cancer cell growth and invasiveness by dual silencing of HER-2 and VEGF.” Molecular pharmaceutics 7.2 (2010): 543-556.
Xu, et al., “Delivery systems for siRNA drug development in cancer therapy”, Asian Journal of Pharmaceutical Sciences, Aug. 28, 2014, vol. 10, No. 1, pp. 1-12.
Zhang et al., “Synthesis and Biological Evaluation of Bivalent Ligands for the Cannabinoid 1 Receptor” Journal of Medicinal Chemistry, 53, pp. 7048-7060.
Office Action with English translation in Japanese application No. 2022-564505, dated Dec. 18, 2023, in 12 pages.
Heissig et al., “DNA as tunable adaptor for siRNA Polyplex Stabilization and Functionalization”, Molecular Therapy-Nucleic Acids, vol. 5(3):e288 (2016).
Office Action in Canadian application No. 3,177,114, dated Apr. 18, 2024, in 5 pages.
Examination Report in Australian application No. 2021263932, dated Jul. 3, 2024, in 4 pages.
Office Action received in Japanese application No. 2022-564505, dated Jun. 30, 2025.
Search Report and Written Opinion in Singapore application No. 11202254428S, dated Jul. 11, 2025, in 10 pages.

* cited by examiner

Preparation Ligand-conjugated homo-trimer of siRNA targeting Human Huntingtin

MULTIMERIC OLIGONUCLEOTIDES WITH DIVIDED STRANDS

INCORPORATION BY REFERENCE TO ANY PRIORITY APPLICATIONS

Any and all applications for which a foreign or domestic priority claim is identified in the PCT Request as filed with the present application are hereby incorporated by reference.

SEQUENCE LISTING IN ELECTRONIC FORMAT

The present application includes a Sequence Listing submitted electronically in XML format. The Sequence Listing is provided as a file entitled MPEG013C1SEQLIST.xml, created on Jan. 20, 2023, which is 8,241 bytes in size. The information in the electronic format of the Sequence Listing is incorporated herein by reference in its entirety.

FIELD OF THE DISCLOSURE

The present disclosure relates to multimeric oligonucleotides. More specifically, the present disclosure relates to multimeric oligonucleotides with divided strands, methods of synthesizing multimeric oligonucleotides using divided strands, and methods of using the resulting oligonucleotides.

BACKGROUND

Oligonucleotides are now a well-established class of therapeutics with multiple applications and ongoing clinical trials. However, many factors still limit the development and use of oligonucleotide therapeutics, for example, the delivery of the oligonucleotide to a target cell and the subsequent internalization of the oligonucleotide into the target cell in sufficient quantities to achieve a desired therapeutic effect.

To address this issue, oligonucleotides conjugated to ligands targeting specific cell surface receptors have been investigated. The use of one such ligand, N-acetylgalactosamine (GalNAc), has become a method of choice for oligonucleotide delivery to hepatocytes due to its highly specific and efficient binding to the asialoglycoprotein receptor, which is expressed in large numbers on the surface of these cells.

However even with the use of GalNAc-conjugated oligonucleotides, a high proportion of the compound is lost via excretion through the kidney. To counter this, multimers of oligonucleotides have been prepared wherein individual oligonucleotide subunits have been linked together via covalently bonded intermediates or "linkers". These linkers have been introduced on the synthesizer or in aqueous solution after synthesis, deprotection and purification of the oligonucleotide.

A variety of linkers have been employed, including ones that are stable under in vivo conditions and others that are cleaved inside the target cell thereby liberating the individual oligonucleotide subunits. The most common type of cleavable linkers used have been short sequences of single-stranded unprotected nucleotides such as dTdTdTdT (SEQ ID NO: 1) and dCdA (SEQ ID NO: 2), which are cleaved by intracellular nucleases, and disulfide-based linkers which are cleaved by the reductive environment inside the cell.

Another technique that has been successfully employed in the synthesis of multimeric oligonucleotides is asymmetric annealing whereby a single-stranded oligonucleotide bonded via a linker to another oligonucleotide is annealed to a complementary single-stranded oligonucleotide, optionally also bonded via a linker to another oligonucleotide, these steps being repeated until a multimer of the desired length is obtained.

Both homo- and hetero-multimers have been prepared via these methods and multimers in the 4-mer to 8-mer range exhibit notably enhanced serum half-lives and bioactivities.

However, these methods have limitations. Nuclease cleavable linkers can only be introduced via the synthesizer. Disulfide linkages can be introduced both on the synthesizer and in aqueous solution after purification of the precursor. However, it is not possible to maintain an internal disulfide group in a multimer while simultaneously reducing a terminal disulfide to a thiol for subsequent linking reactions. Finally, the asymmetric annealing method is difficult to apply to homo-multimers as random polymerization may occur.

There is, therefore, a need for additional methods and materials for use in the assembly and synthesis of multimeric oligonucleotides.

SUMMARY OF THE DISCLOSURE

The present disclosure relates to multimeric oligonucleotides comprising oligonucleotide subunits joined together by covalent linkers, wherein at least one subunit comprises a "partial oligonucleotide."

A partial oligonucleotide is an abbreviated version of an intact or full-length oligonucleotide. In parts of the disclosure, an intact or full-length single-stranded oligonucleotide is represented as "———" and a partial single-stranded oligonucleotide is represented as "—" In many embodiments of the disclosure, an intact or full-length oligonucleotide strand and two partial oligonucleotide strands are complementary, and together are anneal to form a double-stranded oligonucleotide subunit of the multimeric oligonucleotides of the disclosure.

In the context of a double-stranded siRNA, the full-length or intact sense strand of the siRNA might be 21 bases, whereas a partial sense strand might be 10 bases (e.g., the first 10 bases from the 5' end of the full-length sense strand) or the next 11 bases to the 3' end of the full length strand. In parts of the disclosure and its Figures, a full-length or intact sense stranded of an oligonucleotide is represented as 5'-Sense-3' and the partial sense strands are represented as 5'-Se-3' or 5'-nse-3'.

The present disclosure also relates to new synthetic intermediates and methods of synthesizing the multimeric oligonucleotides disclosed herein.

The present disclosure also relates to methods of using the multimeric oligonucleotides, for example in modulating gene expression, biological research, treating or preventing medical conditions, and/or to produce new or altered phenotypes.

The disclosure provides a multimeric oligonucleotide comprising subunits, wherein:

- each of the subunits independently comprises a single-stranded or double-stranded oligonucleotide;
- each of the subunits is joined to another subunit by a covalent linker; and
- at least one subunit comprises at least one partial single-stranded oligonucleotide.

In an embodiment of the multimeric oligonucleotide, at least one subunit comprises two partial single-stranded oligonucleotides annealed to a complementary strand to form a double-stranded subunit.

In an embodiment, the multimeric oligonucleotide comprises Structure 1:

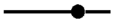 (Structure 1), wherein:

——— is a single-stranded oligonucleotide;

— is a partial single-stranded oligonucleotide; and

• is a covalent linker.

In an embodiment, the multimeric oligonucleotide comprises Structure 2:

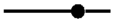 (Structure 2), wherein:

——— is a single-stranded oligonucleotide;

— is a partial single-stranded oligonucleotide; and

• is a covalent linker.

In an embodiment, the multimeric oligonucleotide comprises Structure 3:

(Structure 3), wherein:

Each — is independently a partial single-stranded oligonucleotide; and

• is a covalent linker.

In an embodiment, Structure 3 is a homodimer. In another embodiment, Structure 3 is a heterodimer.

In an embodiment, the multimeric oligonucleotide comprises at least one subunit comprising Structure 4:

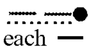 (Structure 4), wherein:

each — is a partial single-stranded oligonucleotide;

• is a covalent linker joined to a partial single-stranded oligonucleotide and an adjoining oligonucleotide subunit; and ............... is a complementary strand.

In an embodiment, the multimeric oligonucleotide comprises Structure 5:

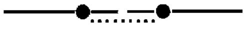 (Structure 5), wherein:

each ———●— is a single-stranded oligonucleotide;

each — is a partial single-stranded oligonucleotide;

each • is a covalent linker joining a single-stranded oligonucleotide to a partial single-stranded oligonucleotide; and ............... is a complementary strand.

In an embodiment, the multimeric oligonucleotide comprises Structure 6:

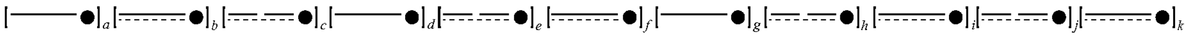

wherein:

each ______ is a single-stranded oligonucleotide;

each — is a partial single-stranded oligonucleotide;

each • is a covalent linker joining adjacent oligonucleotides;

each ............... is a complementary strand; and each of a, b, c, d, e, f, g, h, i, j and k is independently an integer greater than or equal to zero, with the proviso that at least one of c, e, h, and j is greater than or equal to 1. In an embodiment, each of a, b, c, d, e, f, g, h, i, j and k is independently an integer in the range of 0 to 10, with the proviso that at least one of c, e, h and j is greater than or equal to 1.

In an embodiment, the multimeric oligonucleotide comprises Structure 7:

(Structure 7)

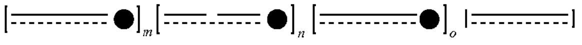

wherein:

———●— are each a single-stranded oligonucleotide;

............... are each a complementary strand;

— are each a partial single-stranded oligonucleotide;

• are each a covalent linker;

m and n are each independently an integer greater than or equal to 1; and o is an integer greater than or equal to zero. In an embodiment, m and n are each independently an integer in the range of 1 to 10 and o is an integer in the range of 0 to 10.

In an embodiment, the multimeric oligonucleotide comprises Structure 8:

(Structure 8)

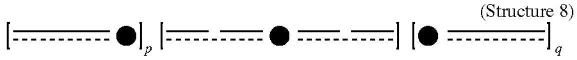

wherein:

——— are each a single-stranded oligonucleotide;

............... are each a complementary strand;

— are each a partial single-stranded oligonucleotide;

• are each a covalent linker; and p and q are each independently an integer greater than or equal to zero. In an embodiment, p and q are each independently an integer in the range of 0 to 10. In an embodiment, p and q are each independently an integer in the range of 0 to 3.

In an embodiment, the multimeric oligonucleotide comprises Structure 9:

(Structure 9)

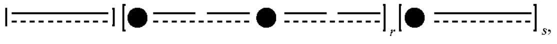

wherein:

——— are each a single-stranded oligonucleotide;

............... are each a complementary strand;

— are each a partial single-stranded oligonucleotide;

• are each a covalent linker;

r is an integer greater than or equal to 1; and s is an integer greater than or equal to zero. In an embodiment, r is an integer in the range of 1 to 10 and s is an integer in the range of 0 to 10. In an embodiment, r is an integer in the range of 1 to 3 and s is 0 or 1.

In an embodiment, the multimeric oligonucleotide comprises Structure 10:

(Structure 10)

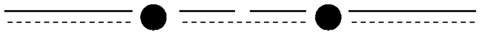 , wherein:

each ——— is a single-stranded oligonucleotide;

each — is a partial single-stranded oligonucleotide;

each • is a covalent linker joining adjacent oligonucleotides; and each ............... is a complementary strand.

In an embodiment, the multimeric oligonucleotide comprises Structure 11:

(Structure 11)

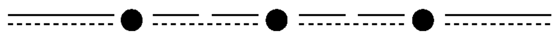, wherein:
each ——— is a single-stranded oligonucleotide;
each — is a partial single-stranded oligonucleotide;
each • is a covalent linker joining adjacent oligonucleotides;
each ……… is a complementary strand.

In an embodiment, the multimeric oligonucleotide comprises Structure 12:

wherein:
each ——— is a single-stranded oligonucleotide;
each — is a partial single-stranded oligonucleotide;
each • is a covalent linker joining adjacent oligonucleotides; and
each ……… is a complementary strand.

In an embodiment, the multimeric oligonucleotide comprises Structure 16:

(Structure 16)

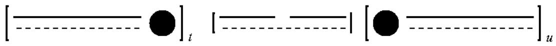

wherein each ——— is a single-stranded oligonucleotide; each (Structure 12)

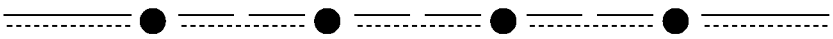, wherein:
each ——— is a single-stranded oligonucleotide;
each — is a partial single-stranded oligonucleotide;
each • is a covalent linker joining adjacent oligonucleotides; and
each ……… is a complementary strand.

In an embodiment, the multimeric oligonucleotide comprises Structure 13:

……… is a complementary strand; each
— is a partial single-stranded oligonucleotide; and
t and u are each independently an integer greater than or equal to 0 with the proviso that at least one oft and u are an integer greater than or equal to 1. In an embodiment, t and u are each independently an integer in the range of 0 to 10 with the proviso that at least one of t and u are an integer greater than or equal to 1. In an embodi- (Structure 13)

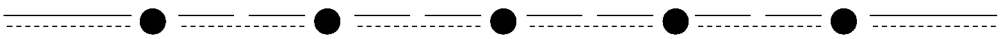, wherein:
each ——— is a single-stranded oligonucleotide;
each — is a partial single-stranded oligonucleotide;
each • is a covalent linker joining adjacent oligonucleotides; and
each ……… is a complementary strand.

In an embodiment, the multimeric oligonucleotide comprises Structure 14:

ment, t and u are each independently an integer in the range of 0 to 3 with the proviso that at least one oft and u are an integer greater than or equal to 1.

In an embodiment of the multimeric oligonucleotide, each partial single-stranded oligonucleotide is 5-14 nucleotides in length.

(Structure 14)

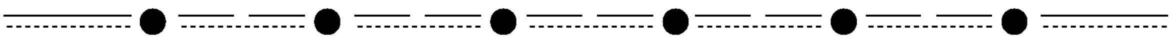, wherein:
each ——— is a single-stranded oligonucleotide;
each — is a partial single-stranded oligonucleotide;
each • is a covalent linker joining adjacent oligonucleotides; and
each ……… is a complementary strand.

In an embodiment, the multimeric oligonucleotide comprises Structure 15:

In an embodiment of the multimeric oligonucleotide, at least two subunits are active against different cellular targets. In an embodiment, all of the subunits are active against different cellular targets.

In an embodiment of the multimeric oligonucleotide, at least two subunits are active against the same cellular target. In an embodiment, all of the subunits are active against the same cellular target.

(Structure 15)

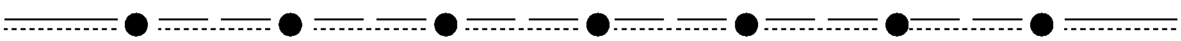,

In an embodiment, each nucleic acid in the multimeric oligonucleotide is RNA, DNA, or an artificial or non-natural nucleic acid analog.

In an embodiment, each nucleic acid in the multimeric oligonucleotide is RNA, DNA, or an artificial or non-natural nucleic acid analog.

In an embodiment of the multimeric oligonucleotide, at least one subunit is siRNA, saRNA, or miRNA.

In an embodiment of the multimeric oligonucleotide, all of the subunits are siRNA.

In an embodiment of the multimeric oligonucleotide, all of the subunits are saRNA.

In an embodiment of the multimeric oligonucleotide, all of the subunits are miRNA.

In an embodiment of the multimeric oligonucleotide, at least one subunit is a single-stranded subunit.

In an embodiment of the multimeric oligonucleotide, at least one single-stranded subunit is an antisense oligonucleotide.

In an embodiment of the multimeric oligonucleotide, at least one covalent linker comprises a cleavable covalent linker.

In an embodiment, one or more of the at least one cleavable covalent linker contains an acid cleavable bond, a reductant cleavable bond, a bio-cleavable bond, or an enzyme cleavable bond.

In an embodiment, the covalent linker is cleavable under intracellular conditions.

In an embodiment, the covalent linkers are each, independently, a disulfide bond or a compound of Structure 25:

(Structure 25)

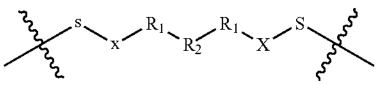

wherein:

S is attached by a covalent bond or by a linker to an oligonucleotide subunit;

each $R_1$ is independently a $C_2$-$C_{10}$ alkyl, $C_2$-$C_{10}$ alkoxy, or $C_1$-$C_{10}$ aryl group;

$R_2$ is a thiopropionate or disulfide group; and each X is independently selected from:

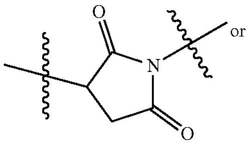

or

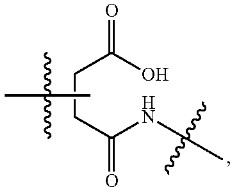

, the latter structure being a composite structure representing the two possible "ring-opened" positional isomers, which are derivatives of succinamic acid.

In an embodiment, the compound of Structure 25 is

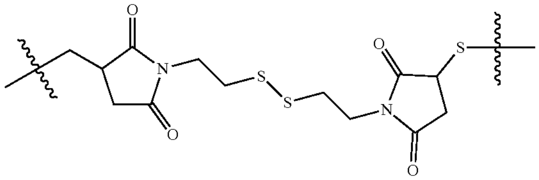 [SMILES: *CC1CC(=O)N(CCSSCCN2C(=O)CC(S*)C2=O)C1=O]

wherein each terminal S is attached by a covalent bond or by a linker to an oligonucleotide subunit.

In an embodiment, the compound of Structure 25 is a compound according to Structure 26:

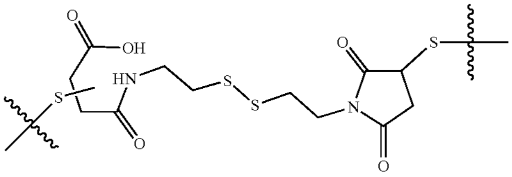

, wherein each terminal S is attached by a covalent bond or by a linker to an oligonucleotide subunit; and wherein the open-ring in Structure 26 is a composite structure representing the two possible ring-opened positional isomers, which are derivatives of succinamic acid.

In an embodiment, the compound of Structure 25 is a compound according to Structure 27:

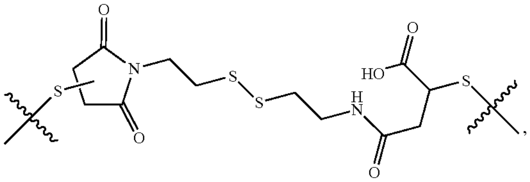

, wherein each terminal S is attached by a covalent bond or by a linker to an oligonucleotide subunit; and wherein the open-ring in Structure 27 is a composite structure representing the two possible ring-opened positional isomers, which are derivatives of succinamic acid.

In an embodiment, the compound of Structure 25 is a compound according to Structure 28:

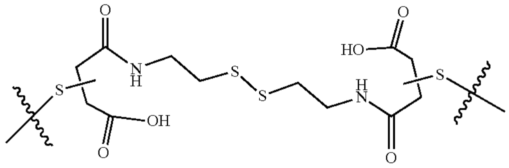

, wherein each terminal S is attached by a covalent bond or by a linker to an oligonucleotide subunit; and wherein the open-ring structures in Structure 28 are composite structures, each of which represents the two possible ring-opened positional isomers, which are derivatives of succinamic acid.

In an embodiment, the covalent linker of Structure 25 is formed from a covalent linker precursor of Structure 29:

(Structure 29)

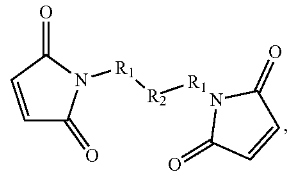

wherein each R1 is independently a $C_2$-$C_{10}$ alkyl, $C_2$-$C_{10}$ alkoxy, or $C_1$-$C_{10}$ aryl group; and R2 is a thiopropionate or disulfide group.

In an embodiment, at least one covalent linker in a multimeric oligonucleotide is attached to the 3' or 5' terminus of an oligonucleotide subunit. In an embodiment, all covalent linkers in a compound or multimeric oligonucleotide are attached to the 3' or 5' terminus of an oligonucleotide subunit.

In an embodiment, at least one covalent linker is attached to an internal nucleotide of an oligonucleotide subunit.

In an embodiment, at least one covalent linker • comprises a nucleotide linker. In an embodiment, the nucleotide linker is between 2-6 nucleotides in length. In an embodiment, the nucleotide linker is UpUpUp (SEQ ID NO: 9), wherein "U" is Uridine and "p" is phosphate. In an embodiment, the nucleotide linker is dTpdTpdTpdTp (SEQ ID NO: 10), wherein "dT" is Thymidine and "p" is phosphate.

In an embodiment of the multimeric oligonucleotide, each covalent linker • is the same. In an embodiment, of the multimeric oligonucleotide, each covalent linker • is different.

In an embodiment, at least two subunits are joined by a covalent linker • between the 3' end of a first subunit and the 3' end of a second subunit. In an embodiment, at least two subunits are joined by a covalent linker • between the 5' end of a first subunit and the 3' end of a second subunit. In an embodiment, at least two subunits are joined by a covalent linker • between the 5' end of a first subunit and the 5' end of a second subunit.

In an embodiment, the multimeric oligonucleotide further comprises a chemical or biological compound that is not an oligonucleotide In an embodiment, the compound or multimeric oligonucleotide is at least 75, 80, 85, 90, 95, 96, 97, 98, 99, or 100% pure.

The disclosure provides a method of synthesizing a multimeric oligonucleotide comprising Structure 16:

(Structure 16)

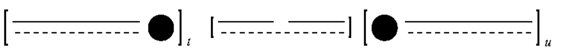

wherein each ——— is a single-stranded oligonucleotide, each — is a partial single-stranded oligonucleotide, each .............. is a complementary strand; each • is a covalent linker joining adjacent oligonucleotides, and t and u are each independently an integer greater than or equal to 1;

the method comprising annealing Structure 17

(Structure 17)

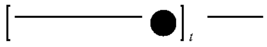

and Structure 18

(Structure 18)

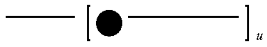

with complementary strands .............., thereby forming Structure 16. In an embodiment, t and u are each independently an integer in the range of 1 to 10. In an embodiment, t and u are each independently an integer in the range of 1 to 3.

In an embodiment, the present disclosure provides a method of synthesizing a multimeric oligonucleotide comprising Structure 8:

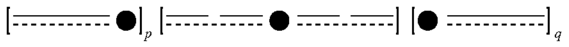

wherein each ——— is a single-stranded oligonucleotide, each — is a partial single-stranded oligonucleotide, each .............. is a complementary strand; each • is a covalent linker joining adjacent oligonucleotides, and p and q are each independently an integer greater than or equal to 1;

the method comprising annealing Structure 19, (Structure 19)

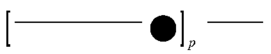

Structure 20, (Structure 20)

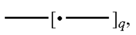

and one or more of Structure 21, (Structure 21)

with complementary strands .............., thereby forming Structure 8. In an embodiment, p and q are each independently an integer in the range of 1 to 10. In an embodiment, p and q are each independently an integer in the range of 1 to 3.

In an embodiment, the present disclosure provides a method of synthesizing a multimeric oligonucleotide comprising Structure 9A:

(Structure 9A)

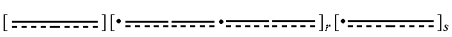

wherein each ——— is a single-stranded oligonucleotide, each — is a partial single-stranded oligonucleotide, each .............. is a complementary strand; each • is a covalent linker joining adjacent oligonucleotides; and r and s are each independently an integer greater than or equal to 1;

the method comprising annealing Structure 22, (Structure 22)

Structure 23

(Structure 23)

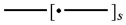

and one or more of Structure 24

(Structure 24)

with complementary strands .............. thereby forming Structure 9A. In an embodiment, r and s are each independently an integer in the range of 1 to 10. In an embodiment, r and s are each independently an integer in the range of 1 to 3.

In an embodiment, the present disclosure provides a method of synthesizing a multimeric oligonucleotide comprising Structure 9B:

(Structure 9B)

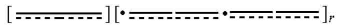

wherein each ——— is a single-stranded oligonucleotide, each — is a partial single-stranded oligonucleotide, each .............. is a complementary strand; each • is a covalent linker joining adjacent oligonucleotides; and r is an integer greater than or equal to 1;

the method comprising annealing Structure 22, (Structure 22)

one or more of Structure 24

(Structure 24)

and a partial single-stranded oligonucleotide — with complementary strands .............., thereby forming Structure 9B. In an embodiment, r is an integer in the range of 1 to 10. In an embodiment, r is an integer in the range of 1 to 3.

The disclosure provides a composition comprising a multimeric oligonucleotide and a pharmaceutically acceptable excipient.

The disclosure provides for the use of multimeri oligonucleotide in the manufacture of a medicament.

The disclosure provides for the treatment of a subject comprising administering to the subject an effective amount of a multimeric oligonucleotide.

These and other embodiments are described in greater detail below.

DETAILED DESCRIPTION

Oligonucleotide Subunits

Figure 1:
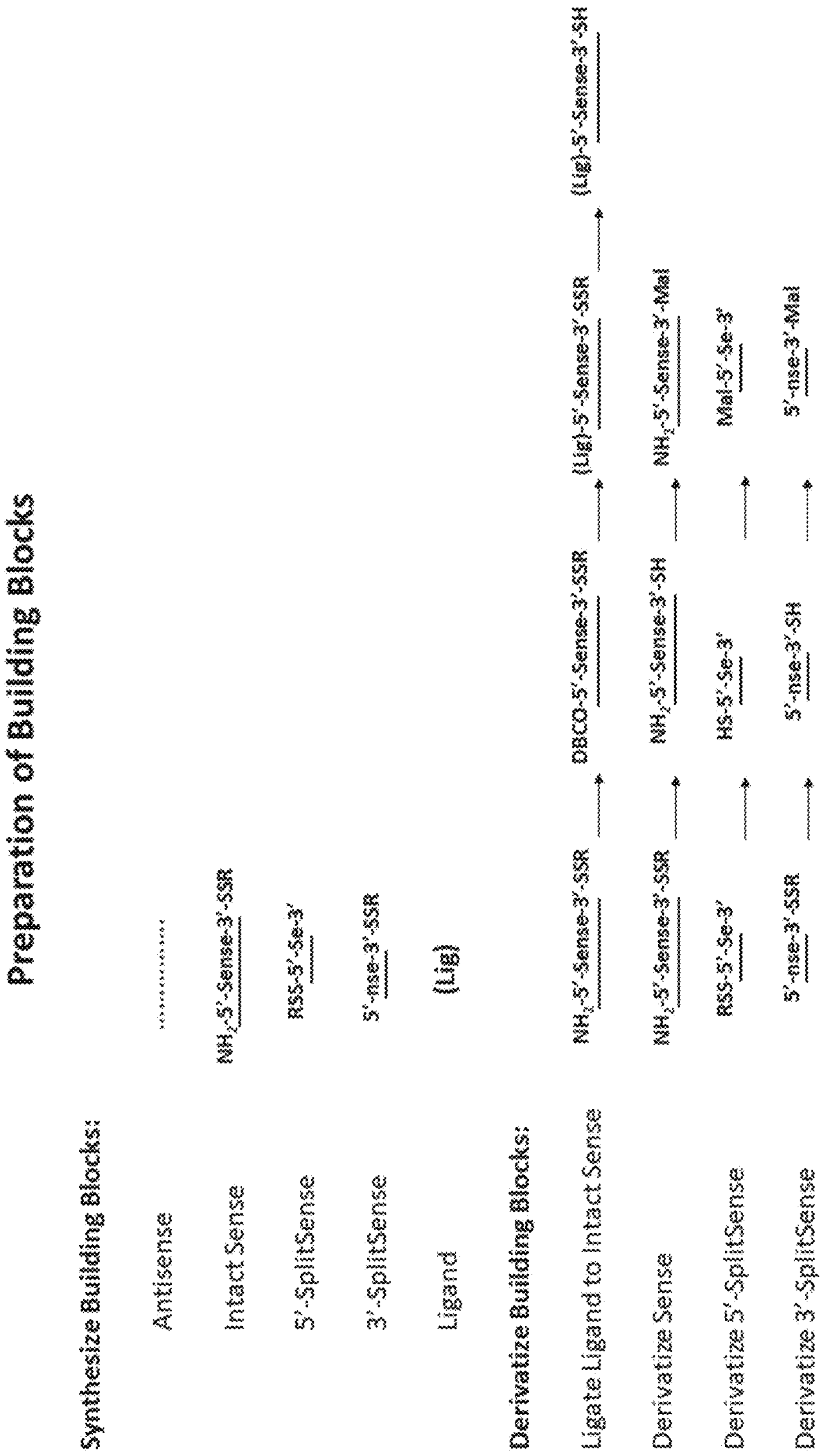
FIG. 1 illustrates various synthetic building blocks and schemes for derivatizing building blocks that are useful for preparing multimeric oligonucleotides according to the present disclosure. In the illustrated embodiments, the intact Sense strand, 5'-SplitSense strand and 3'-SplitSense strand are each derivatized to contain a maleimide (Mal) end group, which is capable of reacting with a thiol group.

The multimeric oligonucleotides described herein are comprised of two or more oligonucleotide subunits joined by one or more covalent linkers. The oligonucleotide subunits include but are not limited to RNA, DNA, a combination thereof, or may comprise an artificial or non-natural nucleic acid analog. In various embodiments, the oligonucleotide is single-stranded. In various embodiments, the oligonucleotide is double-stranded (e.g., antiparallel double-stranded).

Double-stranded oligonucleotide subunits are formed from complementary strands. In this disclosure, a double-stranded oligonucleotide subunit may comprise two intact or full-length complementary strands; or a double-stranded oligonucleotide subunit may comprise two partial strands annealed to a full-length complementary strand. Complementarity can be 100% complementary, or less than 100% complementary where the oligonucleotide nevertheless hybridizes and remains double-stranded under relevant conditions (e.g., physiologically relevant conditions). For example, a double-stranded oligonucleotide can be at least about 80%, 85%, 90%, or 95% complementary. In some embodiments, the double-stranded oligonucleotide is blunt-ended (a symmetric oligonucleotide). In some embodiments, the double-stranded oligonucleotide has a terminal overhang on one strand (e.g., 2-5 overhanging nucleotides) or a terminal overhang on each of its strands (in each case, an asymmetric oligonucleotide).

In each instance in which a structure or embodiment contains two partial single-stranded oligonucleotides annealed to a full-length complementary strand, it may be the case that (A) each of the nucleotides in the full-length complementary strand is paired with a nucleotide in one or the other of the partial oligonucleotide strands, in which case the partial oligonucleotides together represent a "nicked" version of a complementary strand; or (B) some of the nucleotides in the full-length complementary strand are not paired with a nucleotide in one or the other of the partial oligonucleotides, in which case the partial oligonucleotides together represent a "gap" version of a complementary strand. In either case (A) or case (B), the complementary strand will have sufficient complementarity to the partial single-stranded oligonucleotides with which it is paired to form a double-stranded structure. Details concerning the structure of various internally segmented siRNA monomers are disclosed in U.S. Pat. No. 8,329,888 B2, which is incorporated by reference herein in its entirety.

In all of the structures depicted throughout the disclosure, unless otherwise stated, each of the oligonucleotides (whether full-length or partial) is not limited to a single orientation and may be interpreted as having a 5' to 3' orientation or a 3' to 5' orientation and may be linked to another oligonucleotide (whether full-length or partial) via its 5' or 3' end.

The disclosure is applicable to all types of oligonucleotides, double-stranded and single-stranded, including for example, small interfering RNA (siRNA), small activating RNA (saRNA), miRNA, piwi-interacting RNA (piRNA), antisense oligonucleotides in all variations, aptamers, and rybozymes.

In various embodiments, the oligonucleotide is RNA, for example an antisense RNA (aRNA), CRISPR RNA (crRNA), long noncoding RNA (lncRNA), microRNA (miRNA), piwi-interacting RNA (piRNA), small interfering RNA (siRNA), messenger RNA (mRNA), short hairpin RNA (shRNA), small activating (saRNA), or ribozyme.

In various embodiments, the oligonucleotide is a DNA or RNA aptamer.

In some embodiments, the oligonucleotide is a CRISPR guide RNA, or other RNA associated with or essential to forming a ribonucleocomplex (RNP) with a Cas nuclease in vivo, in vitro, or ex vivo, or associated with or essential to performing a genomic editing or engineering function with a Cas nuclease, including for example wild-type Cas nuclease, or any of the known modifications of wild-type Cas, such as nickases and dead Cas (dCas). CRISPR-Cas systems are described, for example, in U.S. Pat. No. 8,771,945; Jinek et al., Science, 337(6096): 816-821 (2012), and International Patent Application Publication No. WO 2013/176772.

In some embodiments, the oligonucleotide is DNA, for example an antisense DNA (aDNA) (e.g., antagomir) or antisense gapmer. Examples of aDNA, including gapmers and multimers, are described for example in Subramanian et al., Nucleic Acids Res, 43(19): 9123-9132 (2015) and International Patent Application Publication No. WO 2013/040429. Examples of antagomirs are described for example, in U.S. Pat. No. 7,232,806.

In various embodiments, the oligonucleotide according to the disclosure further comprises a chemical modification. The chemical modification can comprise a modified nucleoside, modified backbone, modified sugar, and/or modified terminus.

Modifications may include phosphorus-containing linkages, which include but are not limited to phosphorothioates, enantiomerically enriched phosphorothioates, phosphorodithioates, phosphotriesters, aminoalkylphosphotriesters, methyl and other alkyl phosphonates comprising 3' alkylene phosphonates and enantiomerically enriched phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'.

In various embodiments, the oligonucleotides may comprise one or more phosphorothioate groups. The oligonucleotides may comprise one to three phosphorothioate groups at the 5' end. The oligonucleotides may comprise one to three phosphorothioate groups at the 3' end. The oligonucleotides may comprise one to three phosphorothioate groups at the 5' end and the 3' end. In various embodiments, each oligonucleotide contained in the multi-conjugate may comprise 1-10 total phosphorothioate groups. In certain embodiments, each oligonucleotide may comprise fewer than 10, fewer than 9, fewer than 8, fewer than 7, fewer than 6, fewer than 5, fewer than 4, or fewer than 3 total phosphorothioate groups. In certain embodiments, the oligonucleotides contained in the multi-conjugate may possess increased in vivo activity with fewer phosphorothioate groups relative to the same oligonucleotides in monomeric form with more phosphorothioate groups.

The oligonucleotides may be modified using various strategies known in the art to produce a variety of effects, including, e.g., improved potency and stability in vitro and in vivo. Among these strategies are: artificial nucleic acids, e.g., 2'-O-methyl-substituted RNA; 2'-fluro-2' deoxy RNA, peptide nucleic acid (PNA); morpholinos; locked nucleic acid (LNA); Unlocked nucleic acids (UNA); bridged nucleic acid (BNA); glycol nucleic acid (GNA); and threose nucleic acid (TNA); or more generally, nucleic acid analogs, e.g., bicyclic and tricyclic nucleoside analogs, which are structurally similar to naturally occurring RNA and DNA but have alterations in one or more of the phosphate backbone, sugar, or nucleobase portions of the naturally-occurring molecule. Typically, analogue nucleobases confer, among other things, different base pairing and base stacking properties. Examples include universal bases, which can pair with all four canon bases. Examples of phosphate-sugar backbone analogues include, but are not limited to, PNA. Morpholino-based oligomeric compounds are described in Braasch et al., Biochemistry, 41(14): 4503-4510 (2002) and U.S. Pat. Nos. 5,539,082; 5,714,331; 5,719,262; and 5,034,506.

In the manufacturing methods described herein, some of the oligonucleotides are modified at a terminal end by substitution with a chemical functional group. The substitution can be performed at the 3' or 5' end of the oligonucleotide, and may be performed at the 3' ends of both the sense and antisense strands of the monomer, but is not always limited thereto. The chemical functional groups may include, e.g., a sulfhydryl group (—SH), a carboxyl group (—COOH), an amine group (—NH2), a hydroxy group (—OH), a formyl group (—CHO), a carbonyl group (—CO—), an ether group (—O—), an ester group (—COO—), a nitro group (—NO2), an azide group (—N3), or a sulfonic acid group (—SO3H).

The oligonucleotides may be modified to, additionally or alternatively, include nucleobase (referred to in the art simply as "base") modifications or substitutions. Modified nucleobases include nucleobases found only infrequently or transiently in natural nucleic acids, e.g., hypoxanthine, 6-methyladenine, 5-Me pyrimidines, 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77 (1980); Gebeyehu et al., Nucl. Acids Res, 15: 4513 (1997). A "universal" base known in the art, e.g., inosine or pseudouridine, can also be included. 5-Me-C substitutions can increase nucleic acid duplex stability by 0.6-1.2° C. (Sanghvi, Y. S., in Crooke, S. T. and Lebleu, B., eds., Antisense Research and Applications, CRC Press, Boca Raton, pp 276-278 (1993) and are aspects of base substitutions. Modified nucleobases can include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo, such as 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine. Hydroxy group (—OH) at a terminus of the nucleic acid can be substituted with a functional group such as sulfhydryl group (—SH), carboxyl group (—COOH) or amine group (—NH2). The substitution can be performed at the 3' end or the 5' end.

Covalent Linkers.

The covalent linkers present in the multimeric oligonucleotides and used in the synthesis of multimeric oligonucleotides may be cleavable or noncleavable. Cleavable linkers may be selected or designed to maintain stability upon administration, while cleaving upon delivery, or under intracellular conditions, to facilitate functional delivery of the individual oligonucleotide subunits of the multimeric oligonucleotide. In addition to the examples of covalent linkers provided herein, those having ordinary skill will recognize that a wide variety of covalent linkers, including their composition, synthesis, and use are known in the art, and may be adapted for use consistent with this disclosure.

Nucleotide linkers are one example of a class of covalent linkers, including for example, nucleic acid sequences such as Uridine-Uridine-Uridine (UUU) (SEQ ID NO: 3), the endonuclease cleavable linker dCdA (SEQ ID NO: 2), and dTdTdTdT (SEQ ID NO: 1). Nucleotide linkers contain one or more nucleotides selected such that the sequence does not carry out any other designated function. In various aspects of the disclosure, a covalent linker can comprise a nucleotide linker of 2-6 nucleotides in length.

In various aspects of the disclosure, a covalent linker comprises the reaction product of nucleophilic and electrophilic groups. For example, a covalent linker can comprise the reaction product of a thiol and maleimide, a thiol and vinylsulfone, a thiol and pyridyldisulfide, a thiol and iodoacetamide, a thiol and acrylate, an azide and alkyne, or an amine and carboxyl group. As described herein, one of these groups is connected, e.g., to a substituent of the multi-conjugate (e.g., a thiol (—SH) functionalization on the substituent) and the other group presents on a second molecule (e.g., a linking agent) that ultimately links two oligonucleotides (e.g., maleimide in DTME).

Covalent linkers comprising the reaction product of a thiol and maleimide, include but are not limited to DTME (dithiobismaleimidoethane), BM(PEG)2 (1,8-bis(maleimido)diethylene glycol), BM(PEG)3 (1,11-bismaleimido-triethyleneglycol), BMOE (bismaleimidoethane), BMH (bismaleimidohexane), or BMB (1,4-bismaleimidobutane). DTME is advantageous in that it contains an internal disulfide which is cleavable intracellularly, in the reductant environment of the cytosol.

In various aspects of the disclosure, the covalent linker may comprise a non-ionic hydrophilic polymer such as polyethyleneglycol (PEG), polyvinylpyrolidone and polyoxazoline, or a hydrophobic polymer such as PLGA and PLA.

Polymer linking agents used as a mediator for a covalent bond include but are not limited to non-ionic hydrophilic polymers including polyethylene glycol (PEG), Pluronic, polyvinylpyrolidone, polyoxazoline, or copolymers thereof; or one or more biocleavable polyester polymers including poly-L-lactic acid, poly-D-lactic acid, poly-D,L-lactic acid, poly-glycolic acid, poly-D-lactic-co-glycolic acid, poly-L-lactic-co-glycolic acid, poly-D,L-lactic-co-glycolic acid, polycaprolactone, polyvalerolactone, polyhydroxybutyrate, polyhydroxyvalerate, or copolymers thereof.

The linking agent may have a molecular weight of about 100 to 10,000 Daltons. Examples of such linking agents include dithio-bis-maleimidoethane (DTME), 1,8-bis-maleimidodiethyleneglycol (BM(PEG)2), tris-(2-maleimidoethyl)-amine (TMEA), tri-succinimidyl aminotriacetate (TSAT), 3-arm-poly(ethylene glycol) (3-arm PEG), maleimide, N-hydroxysuccinimide (NHS), vinylsulfone, iodoacetyl, nitrophenyl azide, isocyanate, pyridyldisulfide, hydrazide, and hydroxyphenyl azide Linking agents comprising cleavable bonds or noncleavable bonds may be used herein, and indeed, in some instances, may be used together in the same multi-conjugate. Linking agents comprising noncleavable bonds include but are not limited to those comprising an amide bond or a urethane bond. Linking agents comprising cleavable bonds include but are not limited to those comprising an acid cleavable bond (e.g., a covalent bond of ester, hydrazone, or acetal), a reductant cleavable bond (e.g., a disulfide bond), a bio-cleavable bond, or an enzyme cleavable bond (e.g., nucleic acid-based linkers or oligopeptide-based linkers). In some instances, the cleavable covalent linker is cleavable under intracellular conditions. Additionally, any linking agent available for drug conjugation can be used in the foregoing aspects of the invention without limitation.

Further, combinations of functional groups and linking agents may include: (a) where the functional groups are amino or thiol, the linking agent may be Succinimidyl 3-(2-pyridyldithio)propionate, or Succinimydyl 6-([3(2-pyridyldithio)propioamido]hexanoate; (b) where the functional group is amino, the linking agent may be 3,3'dithiodipropionic acid di-(N-succinimidyl ester), Dithio-bis(ethyl 1H-imidazole-1-carboxylate), or Dithio-bis(ethyl 1H-imidazole-1-carboxylate); (c) where the functional groups are amino or alkyne, the linking agent may be Sulfo-N-succinimidyl3-[[2-(p-azidosalicylamido)ethyl]-1,3'-dithio]propionate; and (d) where the functional group is thiol, the linking agent may be dithio-bis-maleimidoethane (DTME), 1,8-Bis-maleimidodiethyleneglycol (BM(PEG)2), or dithiobis (sulfosuccinimidyl propionate) (DTSSP).

In various methods for preparing and synthesizing the synthetic intermediates and multimeric oligonucleotides provided herein, there may be a step involving the activation of a functional group. Compounds that can be used in the activation of functional groups include but are not limited to 1-ethyl-3,3-dimethylaminopropyl carbodiimide, imidazole, N-hydroxysuccinimide, dichlorohexylcarbodiimide, N-beta-Maleimidopropionic acid, N-beta-maleimidopropyl succinimide ester or N-Succinimidyl 3-(2-pyridyldithio)propionate.

Further examples of covalent linkers and methods of making and using them are described in WO2016/205410, WO2018/145086, and WO 2020/180897, each of which is incorporated herein by reference.

Chemical or Biological Compounds.

Any of the multimeric oligonucleotides may comprise a chemical or biological compound that is not an oligonucleotide. Such chemical or biological compounds include but are not limited to amino acids, peptides, proteins, lipids, carbohydrates, carboxylic acids, vitamins, steroids, lignins, small molecules (e.g., a small molecule therapeutic or drug molecule), organometallic compounds, or derivatives of any of the foregoing.

In some aspects of the disclosure, the chemical or biological compound may comprise a cell- or tissue-targeting moiety, such as but not limited to a ligand specific for a given cell-surface receptor. Examples of cell- or tissue-targeting moieties include but are not limited to lipophilic moieties, such as phospholipids; aptamers (of DNA or RNA, or derivatives thereof); peptides and proteins, such as antigen-binding peptides or proteins; small molecules; vitamins, such as tocopherol and folate; other folate receptor-binding ligands; carbohydrates, such as N-Acetylgalactosamine (GalNAc) and mannose; other mannose-receptor binding ligands; cholesterols; carboxylic acids, such as 2-[3-(1,3-dicarboxypropyl)-ureido]pentanedioic acid (DUPA); and derivatives of benzamide, such as anisamide.

A cell- or tissue-targeting lipophilic moiety may comprise a cationic group. In some aspects of the present disclosure, the lipophilic moiety comprises a cholesterol, vitamin E, vitamin K, vitamin A, folic acid, or a cationic dye (e.g., Cy3). Other lipophilic moieties include but are not limited to cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

Examples of antigen-binding proteins include but are not limited to monoclonal antibodies, single chain variable fragments (ScFv) or VHH antigen-binding proteins.

Examples of GalNAc-based biological moieties include but are not limited to mono-antennary GalNAc, di-antennary GalNAc, and tri-antennary GalNAc.

Other biological moieties, some or all of which may have cell- or tissue-targeting properties, include but are not limited to fatty acids, such as cholesterol; Lithocholic acid (LCA); Eicosapentaenoic acid (EPA); Docosahexaenoic acid (DHA); Docosanoic acid (DCA); steroids; secosteroids; lipids; gangliosides; nucleoside analogs; endocannabinoids; vitamins such as choline, vitamin A, vitamin E, retinoic acid and tocopheryl; and derivatives of any of the foregoing.

Other peptide-based biological moieties, some or all of which may have cell- or tissue-targeting properties, include but are not limited to: APRPG (SEQ ID NO: 4), cNGR (CNGRCVSGCAGRC) (SEQ ID NO: 5), F3 (KDEPQRRSARLSAKPAPPKPEPKPKKAPAKK) (SEQ ID NO: 6), CGKRK (SEQ ID NO: 7), and/or iRGD (CRGDKGPDC) (SEQ ID NO: 8).

In various aspects, the disclosure provides for the use and incorporation of nuclear localization signals or sequences (NLS) to facilitate importation of a material to which it is linked or incorporated to the cellular nucleus. The NLS is typically an amino acid sequence, examples of which are known by those working in the field of drug delivery.

In some aspects of the disclosure, a the chemical or biological compound may comprise an endosomal escape moiety (EEM), selected to assist or enable other biologically active moieties with which it is delivered to disrupt the endosomal membrane or otherwise to escape the endosome or other organelle within which the biological moiety is internalized (such as by endocytosis) upon intracellular delivery. Endosomal escape moieties are oftentimes lipid-based or amino acid-based, but may comprise other chemical entities that disrupt an endosome to release its cargo. Examples of EEMs include but are not limited to chloroquine, peptides and proteins with motifs containing hydrophobic amino acid R groups, and influenza virus hemagglutinin (HA2). Further EEMs are described in Lonn et al., Scientific Reports, 6: 32301, 2016.

Other chemical or biological compounds within the scope of the disclosure may comprise a detectable label. As used herein, "detectable label" has its ordinary meaning as understood by those skilled in the art. It refers to a chemical group that is a substituent of a multi-conjugate and detectable by an imaging technique, such as fluorescence spectroscopy. For example, the detectable label may be a dye that comprises a fluorophore, which, after absorption of energy, emits radiation at a defined wavelength. Many suitable fluorescent labels or dyes are known. For example, Welch et al. (Chem. Eur. J. 5(3):951-960, 1999) discloses dansyl-functionalised fluorescent moieties and Zhu et al. (Cytometry 28:206-211, 1997) describes the use of the fluorescent labels Cy3 and Cy5. Other labels are described in Prober et al. (Science 238:336-341, 1987); Connell et al. (BioTechniques 5(4): 342-384, 1987), Ansorge et al. (Nucl. Acids Res. 15(11): 4593-4602, 1987) and Smith et al. (Nature 321:674, 1986). Examples of commercially available fluorescent labels include, but are not limited to, fluorescein, rhodamine (such as TMR, texas red or Rox), alexa, bodipy, acridine, coumarin, pyrene, benzanthracene and cyanine (such as Cy2 or Cy4). Other forms of detectable labels include microparticles, including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci USA 97(17):9461-9466, 2000), and tags detectable by mass spectrometry. The detectable label may be a multi-component label that is dependent on an interaction with another compound for detection, such as the biotin-streptavidin system.

Methods for Treating Disease and for Modulating Gene Expression

The disclosure provides methods for using the disclosed multimeric oligonucleotides for the treatment of diseases or disorders that may be addressed by modulating gene expression, for example by up-regulating, or down-regulating or silencing gene expression, or by affecting mRNA splicing. The teachings of this disclosure will serve to enable persons of skill to design and develop multimeric oligonucleotide for the medical or veterinary treatment of such conditions, or for modulating gene expression in other fields such as basic research, agriculture, diagnostics and animal husbandry. Where multiple gene targets are desired to be affected, the multimeric oligonucleotides of the present disclosure enable multi-targeting to be achieved with a single chemical entity.

In one aspect, the disclosure provides a method for treating a subject with a disease or disorder that would benefit from modulating gene expression, the method comprising administering an effective amount of a multimeric oligonucleotide according to the disclosure to the subject.

In one aspect, the disclosure provides a method for modulating gene expression of a target gene, comprising administering an effective amount of a multimeric oligonucleotide according to the disclosure to a subject. In such therapeutic embodiments, the multimeric oligonucleotide will comprise at least one subunit that modulates gene expression, for example but not limited to an siRNA, a miRNA, a saRNA, or an antisense oligonucleotide, a CRISPR nuclease, a crRNA, and derivatives of any of the foregoing.

Similarly, the disclosure provides a method for modulating expression of two or more target genes comprising administering an effective amount of a multimeric oligonucleotide according to the disclosure to a subject, wherein the multimeric oligonucleotide comprises subunits that modulate gene expression in the two or more target genes or gene products.

In all of the foregoing aspects of the disclosure, the multimeric oligonucleotide may include, in addition to the one or more subunits that modify gene expression, other substituents that produce other therapeutic effects, including but not limited to immune stimulation or suppression, check point inhibition, and inflammation reduction. Multi-conjugates comprising substituents that provide multi-therapeutic effects will serve to advance treatments for complex diseases and conditions such as cancer, autoimmune and neurological disorders.

Subjects

Subjects that may benefit from the disclosed methods of treatment and methods of administration disclosed herein include, but are not limited to, mammals, such as primates, rodents, and agricultural animals. Examples of primate subjects include, but are not limited to, humans, chimpanzees, and macaques. Examples of a rodent subject includes, but is not limited to, a mouse and a rat. Examples of an agricultural animal subject includes, but is not limited to, a cow, a sheep, a lamb, a chicken, and a pig.

In this, and other embodiments, the multi-conjugates of the disclosure can be administered to a subject in the form of a pharmaceutical composition, in a delivery vehicle, or coupled to a cell- or tissue-targeting ligand.

Pharmaceutical Compositions

In various aspects, the disclosure provides for pharmaceutical compositions comprising the multimeric oligonucleotides described herein. As used herein, pharmaceutical compositions include active agents, other than foods, that can be used to prevent, diagnose, alleviate, treat, or cure a disease. Similarly, the various multimeric oligonucleotides according to the disclosure should be understood as including embodiments for use as a medicament and/or for use in the manufacture of a medicament.

A pharmaceutical composition can include a multimeric oligonucleotide according to the disclosure and a pharmaceutically acceptable excipient. As used herein, an excipient can be a natural or synthetic substance formulated alongside the active ingredient. Excipients can be included for the purpose of long-term stabilization, increasing volume (e.g., bulking agents, fillers, or diluents), or to confer a therapeutic enhancement on the active ingredient in the final dosage form, such as facilitating drug absorption, reducing viscosity, or enhancing solubility. Excipients can also be useful in manufacturing and distribution, for example, to aid in the handling of the active ingredient and/or to extend shelf-life stability (e.g., by preventing denaturation or aggregation). As will be understood by those skilled in the art, appropriate excipient selection can depend upon various factors, including the route of administration, dosage form, and active ingredient(s).

Multimeric oligonucleotide can be administered in a variety of ways, including but not limited to locally or systemically, and thus the pharmaceutical compositions of the disclosure can vary accordingly. Administration is not limited to any particular delivery route, system, or technique and may include, without limitation, parenteral (including subcutaneous, intravenous, intramedullary, intraarticular, intramuscular, intraperitoneal, intraocular, or CNS injection), rectal, topical, transdermal, oral, or by inhalation (intranasally or to the lungs by way of, e.g., a nebulizer). Administration to an individual may occur in a single dose or in repeat administrations, and in any of a variety of physiologically acceptable salt forms, and/or with an acceptable pharmaceutical carrier and/or additive as part of a pharmaceutical composition. Physiologically acceptable formulations and standard pharmaceutical formulation techniques, dosages, and excipients are well known to persons skilled in the art (see, e.g., Physicians' Desk Reference (PDR®) 2005, 59th ed., Medical Economics Company, 2004; and Remington: The Science and Practice of Pharmacy, eds. Gennado et al. 21th ed., Lippincott, Williams & Wilkins, 2005).

Pharmaceutical compositions include an effective amount of the multimeric oligonucleotide. As used herein, "effective amount" can be a concentration or amount that results in achieving a particular purpose, for example, an amount adequate to cause a biological effect, for example in comparison to a placebo. Where the effective amount is a "therapeutically effective amount," it can be an amount adequate for therapeutic use, for example an amount sufficient to prevent, diagnose, alleviate, treat, or cure a disease. An effective amount can be determined by methods known in the art. For example, a therapeutically effective amount can be determined empirically, for example by human clinical trials. Effective amounts can also be extrapolated from one animal (e.g., mouse, rat, monkey, pig, dog) for use in another animal (e.g., human), using conversion factors known in the art. See, e.g., Freireich et al., Cancer Chemother Reports 50(4):219-244 (1966).

Delivery Constructs and Formulations

As will be understood by those skilled in the art, regardless of biological target or mechanism of action, therapeutic oligonucleotides must overcome a series of physiological hurdles to access a target cell or tissue in an organism (e.g., animal, such as a human, in need of therapy). Therapeutic oligonucleotide generally must avoid clearance in the bloodstream, enter the target cell type, and enter the cytoplasm, and sometimes enter the nucleus, all without eliciting an undesirable immune response. In various aspects, the disclosure provides multimeric oligonucleotides for direct delivery to cell and tissue targets.

In direct delivery strategies, the multimeric oligonucleotides will require stabilization, usually in the form of chemical modification of the substituents, to enable them to withstand degradation by serum nucleases and other factors, and to avoid the triggering of an innate immune response. Chemical stabilization strategies are known to those of skill in the art and may be readily used or adapted in connection with the multimeric oligonucleotides disclosed herein.

In some aspects of the disclosure, multimeric oligonucleotides are equipped with a targeting moiety, such as a cell- or tissue-targeting ligand for direct delivery to a target cell or tissue without the need for formulation in a delivery vehicle. Examples of targeting moieties suitable for use in connection with this disclosure include but are not limited to a lipophilic moiety (e.g., a phospholipid); aptamers; peptides or proteins (e.g., arginine-glycine-aspartic acid [RGD], transferrin, monoclonal antibodies or fragments thereof, such as a single chain variable fragment (ScFv), or a VHH antigen-binding protein); cell growth factors, small molecules, vitamins (e.g., folate, tocopherol), carbohydrates (e.g., monosaccharides and polysaccharides, N-Acetylgalactosamine [GalNAc], galactose, mannose); cholesterol; glutamate ureas (e.g., 2-[3-(1,3-dicarboxypropyl)-ureido]pentanedioic acid [DUPA]), benzamide derivatives (e.g., anisamide); and derivatives of any of the foregoing. In some embodiments, the GalNac targeting moiety may be a mono-antennary GalNAc, a di-antennary GalNAc, or a tri-antennary GalNAc.

The lipophilic moiety may be a ligand that includes a cationic group. In certain embodiments, the lipophilic moiety is a cholesterol, vitamin E, vitamin K, vitamin A, folic acid, or a cationic dye (e.g., Cy3). Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

The targeting moiety may be a fatty acid, such as cholesterol, Lithocholic acid (LCA), Eicosapentaenoic acid (EPA), Docosahexaenoic acid (DHA), and Docosanoic acid (DCA), steroid, secosteroid, lipid, ganglioside or nucleoside analog, endocannabinoid, and/or vitamin such as choline, vitamin A, vitamin E, and derivatives or metabolites thereof, or a vitamin such as retinoic acid and alpha-tocopheryl succinate.

A targeting moiety may be incorporated into a multimeric oligonucleotide using the teachings of this disclosure as well as other techniques known in the art, including but not limited to a covalent bond, an amide bond, or an ester bond, or via a non-covalent bond such as biotin-streptavidin, or a metal-ligand complex.

A targeting moiety can be bound to the multimeric oligonucleotide at a terminal location, or in some instances, at an internal location. In some embodiments, two targeting moieties are incorporated into the multimeric oligonucleotide, e.g., where a targeting moiety is conjugated at each terminus of the multimeric oligonucleotide. More than two targeting moieties may be incorporated into the multimeric oligonucleotide, if desired, and at a variety of locations both internal and terminal.

In various aspects, the disclosure provides for the use and incorporation of endosomal escape moieties (EEMs) to facilitate endosomal escape of a multimeric oligonucleotide that has been endocytosed by a cell. Endosomal escape moieties are generally lipid-based or amino acid-based, but may comprise other chemical entities that disrupt an endosome to release the multimeric oligonucleotide or its metabolites (e.g., subunits of the multimeric oligonucleotide liberated by cleavage of a linker). Examples of EEMs include, but are not limited to, chloroquine, peptides and proteins with motifs containing hydrophobic amino acid R groups, and influenza virus hemagglutinin (HA2). Further EEMs are described in Lonn et al., Scientific Reports, 6: 32301, 2016.

In various aspects, the disclosure provides for the use and incorporation of nuclear localization signals or sequences (NLS) to facilitate importation of the multimeric oligonucleotides or metabolites to the nucleus of a cell to which the multimeric oligonucleotide has been delivered. The NLS is typically an amino acid sequence, examples of which are known by those working in the field of drug delivery.

One skilled in the art will appreciate that known delivery formulations, vehicles and targeting moieties can generally be adapted for use according to the present disclosure. Relevant teachings and examples are disclosed in U.S. Pat. Nos. 9,644,209 and 10,597,659; WO 2016/205410 A2; WO 2018/145086 A1; and WO 2020/180897, each of which are incorporated herein by reference in their entirety.

The following Examples are illustrative and not restrictive. Many variations of the technology will become apparent to those of skill in the art upon review of this disclosure. The scope of the technology should, therefore, be determined not with reference to the Examples, but instead should be determined with reference to the appended claims along with their full scope of equivalents.

EXAMPLES

Example 1: Single Chain Oligonucleotide Synthesis

Oligoribonucleotides were assembled on ABI 394 and 3900 synthesizers (Applied Biosystems) at the 10 μmol scale, or on an Oligopilot 10 synthesizer at 28 μmol scale, using phosphoramidite chemistry. Solid supports were polystyrene loaded with 2'-deoxythymidine (Glen Research, Sterling, Virginia, USA), or controlled pore glass (CPG, 520Å, with a loading of 75 μmol/g, obtained from Prime Synthesis, Aston, PA, USA). Ancillary synthesis reagents, DNA-, 2'-O-Methyl RNA-, and 2'-deoxy-2'-fluoro-RNA phosphoramidites were obtained from SAFC Proligo (Hamburg, Germany). Specifically, 5'-O-(4,4'-dimethoxytrityl)-3'-O-(2-cyanoethyl-N,N-diisopropyl) phosphoramidite monomers of 2'-O-methyl-uridine (2'-OMe-U), 4-N-acetyl-2'-O-methyl-cytidine (2'-OMe-CAc), 6-N-benzoyl-2'-O-methyl-adenosine (2'-OMe-Abz) and 2-N-isobutyrlguanosine (2'-OMe-GiBu) were used to build the oligomer sequences. 2'-Fluoro modifications were introduced employing the corresponding phosphoramidites carrying the same nucleobase protecting groups as the 2'-OMe RNA building blocks. Coupling time for all phosphoramidites (70 mM in Acetonitrile) was 3 min employing 5-Ethylthio-1H-tetrazole (ETT, 0.5 M in Acetonitrile) as activator. Phosphorothioate linkages were introduced using 50 mM 3-((Dimethylamino-methylidene)amino)-3H-1,2,4-dithiazole-3-thione (DDTT, AM Chemicals, Oceanside, California, USA) in a 1:1 (v/v) mixture of pyridine and Acetonitrile. Upon completion of the solid phase synthesis including removal of the DMT group ("DMT off synthesis") oligonucleotides were cleaved from the solid support and deprotected using a 1:1 mixture consisting of aqueous methylamine (41%) and concentrated aqueous ammonia (32%) for 3 hours at 25° C. according to published methods (Wincott, F. et al: Synthesis, deprotection, analysis and purification of RNA and ribozymes. Nucleic Acids Res, 23: 2677-2684 (1995).

Subsequently, crude oligomers were purified by anionic exchange HPLC using a column packed with Source Q15 (GE Healthcare) and an AKTA Explorer system (GE Healthcare). Buffer A was 10 mM sodium perchlorate, 20 mM Tris, 1 mM EDTA, pH 7.4 (Fluka, Buchs, Switzerland) in 20% aqueous Acetonitrile and buffer B was the same as buffer A with 500 mM sodium perchlorate. A gradient of 22% B to 42% B within 32 column volumes (CV) was employed. UV traces at 280 nm were recorded. Appropriate fractions were pooled and precipitated with 3M NaOAc, pH=5.2 and 70% Ethanol. Pellets were collected by centrifugation. Alternatively, desalting was carried out using Sephadex HiPrep columns (GE Healthcare) according to the manufacturer's recommendations.

Oligonucleotides were reconstituted in water and identity of the oligonucleotides was confirmed by electrospray ionization mass spectrometry (ESI-MS). Purity was assessed by analytical anion-exchange HPLC.

Example 2: Generation of Thiol-Terminated siRNA

Where necessary 3'- or 5'-terminal thiol groups were introduced via 1-O-Dimethoxytrityl-hexyl-disulfide, 1'-[(2-cyanoethyl)-(N,N-diisopropyl)]-phosphoramidite linker (NucleoSyn, Olivet Cedex, France). Upon completion of the solid phase synthesis and final removal of the DMT group ("DMT off synthesis") oligonucleotides were cleaved from the solid support and deprotected using a 1:1 mixture consisting of aqueous methylamine (41%) and concentrated aqueous ammonia (32%) for 6 hours at 10° C. Subsequently, the crude oligonucleotides were purified by anion-exchange high-performance liquid chromatography (HPLC) on an AKTA Explorer System (GE Healthcare, Freiburg, Germany). Purified ($C_6SSC_6$)-oligonucleotides were precipitated by addition of ethanol and overnight storage in the freezer. Pellets were collected by centrifugation. Oligonucleotides were reconstituted in water and identity of the oligonucleotides was confirmed by electrospray ionization mass spectrometry (ESI-MS). Purity was assessed by analytical anion-exchange and RP HPLC.

Each disulfide containing oligomer was then reduced using a 100 mM DL-Dithiothreitol (DTT) solution. 1.0 M DTT stock solution (Sigma-Aldrich Chemie GmbH, Munich, Germany, #646563,) was diluted with Triethylammonium bicarbonate buffer (TEABc, 1M, pH 8.5, Sigma, #90360) and water to give a solution 100 mM each in DTT and TEABc. The oligonucleotide was dissolved in TEABc buffer (100 mM, pH 8.5) to yield a 1 mM solution. To accomplish the disulfide reduction a 50-100 fold molar DTT excess was added to the oligonucleotide solution. The progress of the reduction was monitored by analytical AEX HPLC on a Dionex DNA Pac 200 column (4×250 mm) obtained from Thermo Fisher. The reduced material, i.e. the corresponding thiol (C6SH), elutes prior to the starting material. After completion of the reaction, excess reagent was removed by size exclusion chromatography using a HiPrep column from GE Healthcare and water as eluent.

Subsequently, the oligonucleotide was precipitated using 3 M NaOAc (pH 5.2) and ethanol and stored at minus 20° C.

Example 3: Preparation of Mono-DTME Oligomer

Thiol modified oligonucleotide was dissolved in 300 mM NaOAc (pH 5.2) containing 25% acetonitrile to give a 20 OD/mL solution. 40 equivalents dithiobismaleimidoethane (DTME, Thermo Fisher, #22335) were dissolved in acetonitrile to furnish a 15.6 mM solution. The DTME solution was added to the oligonucleotide-containing solution and agitated at 25° C. on a Thermomixer (Eppendorf, Hamburg, Germany). Progress of the reaction was monitored by analytical AEX HPLC using a Dionex DNA Pac200 column (4×250 mm). Depending on the required purity level excess DTME was either removed by size exclusion HPLC using a HiPrep column (GE Healthcare) or the crude reaction mixture was purified by preparative AEX HPLC using a column packed with Source 15 Q resin commercially available from GE Healthcare.

Example 4: Preparation of Dimer Via DTME Functionality

The DTME modified oligonucleotide prepared according to the procedure in Example 2 was reacted with another oligonucleotide equipped with a thiol linker. This reaction could either be carried out on the single stranded sequence or after prior annealing of the complementary oligonucleotide of one of the reaction partners. Consequently, if desired, the DTME modified oligonucleotide was reacted with the thiol modified oligonucleotide directly, or was annealed with its complementary strand and the resulting duplex reacted with the thiol modified oligonucleotide. Alternatively, the thiol modified oligonucleotide was annealed with its complementary strand and this duplex reacted with the DTME modified single strand. In all cases the reaction was carried out in aqueous solution in the presence of 300 mM NaOAc (pH 5.2).

Example 5: Annealing of Single Stranded RNAs (ssRNAs) to Form Double Stranded RNA (dsRNA)

dsRNAs were generated from RNA single strands by mixing equimolar amounts of complementary sense and antisense strands and annealing in 20 mM NaCl/4 mM sodium phosphate pH 6.8 buffer. Successful duplex formation was confirmed by native size exclusion HPLC using a Superdex 75 column (10×300 mm) from GE Healthcare. Samples were stored frozen until use.

Example 6: Preparation of 3'- or 5'-$NH_2$ Derivatized Oligonucleotides

RNA equipped with a C-6-aminolinker at the 5'-end of the sense strand was produced by standard phosphoramidite chemistry on solid phase at a scale of 140 μmol using an ÄKTA Oligopilot 100 (GE Healthcare, Freiburg, Germany) and controlled pore glass (CPG) as solid support (Prime Synthesis, Aston, Pa., USA). Oligomers containing 2"-O-methyl and 2'-F nucleotides were generated employing the corresponding 2'-OMe-phosphoramidites, 2'-F-methyl phosphoramidites. The 5'-aminohexyl linker at the 5'-end of the sense strand was introduced employing the TFA-protected hexylaminolinker phosphoramidite (Sigma-Aldrich, SAFC, Hamburg, Germany). In case the hexylamino-linker was needed at the 3'-position, a phtalimido protected hexylamino-linker immobilized on CPG (Prime Synthesis, Aston, Pa., USA) was used. Cleavage and deprotection was accomplished using a mixture of 41% methylamine in water and concentrated aqueous ammonia (1:1 v/v). Crude oligonucleotides were purified using anion exchange HPLC and a column (2.5×18 cm) packed with Source 15Q resin obtained from GE Healthcare.

Figure 2:
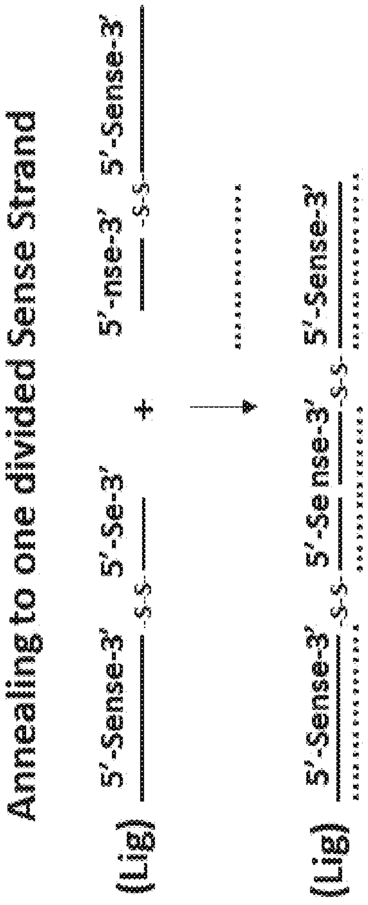
FIG. 2 illustrates a scheme for synthesizing a trimer of double-stranded oligonucleotide subunits, wherein the middle subunit comprises a split sense strand.
Figure 3:
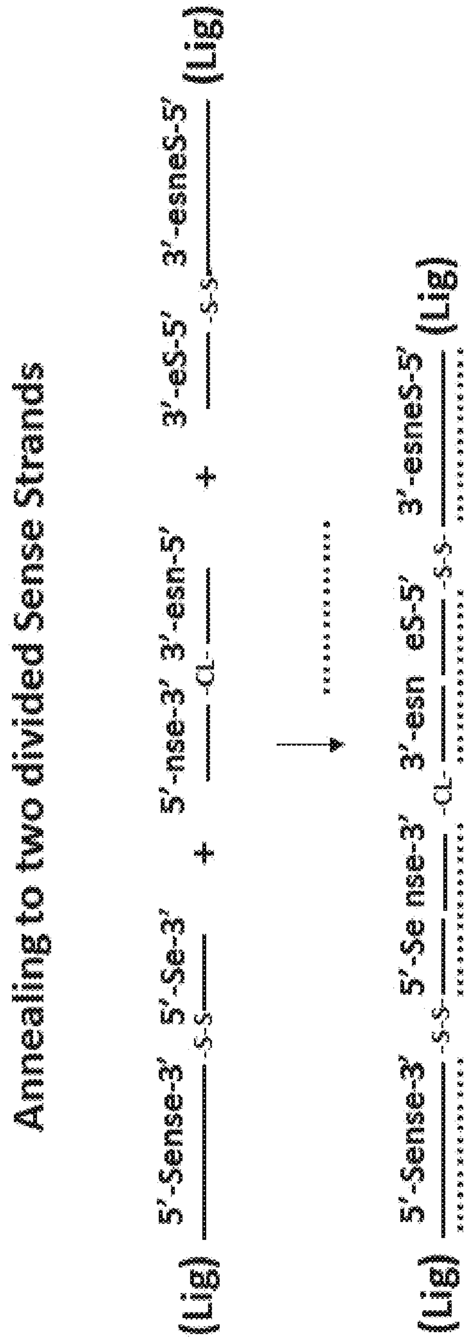
FIG. 3 illustrates a scheme for synthesizing a tetramer of double-stranded oligonucleotide subunits, wherein the middle two subunits each comprise split sense strand. Optionally a cell- or tissue-targeting ligand (Lig) is conjugated to one or both of the terminal subunits. The symbol —CL- represents a cleavable linker.
Figure 4:
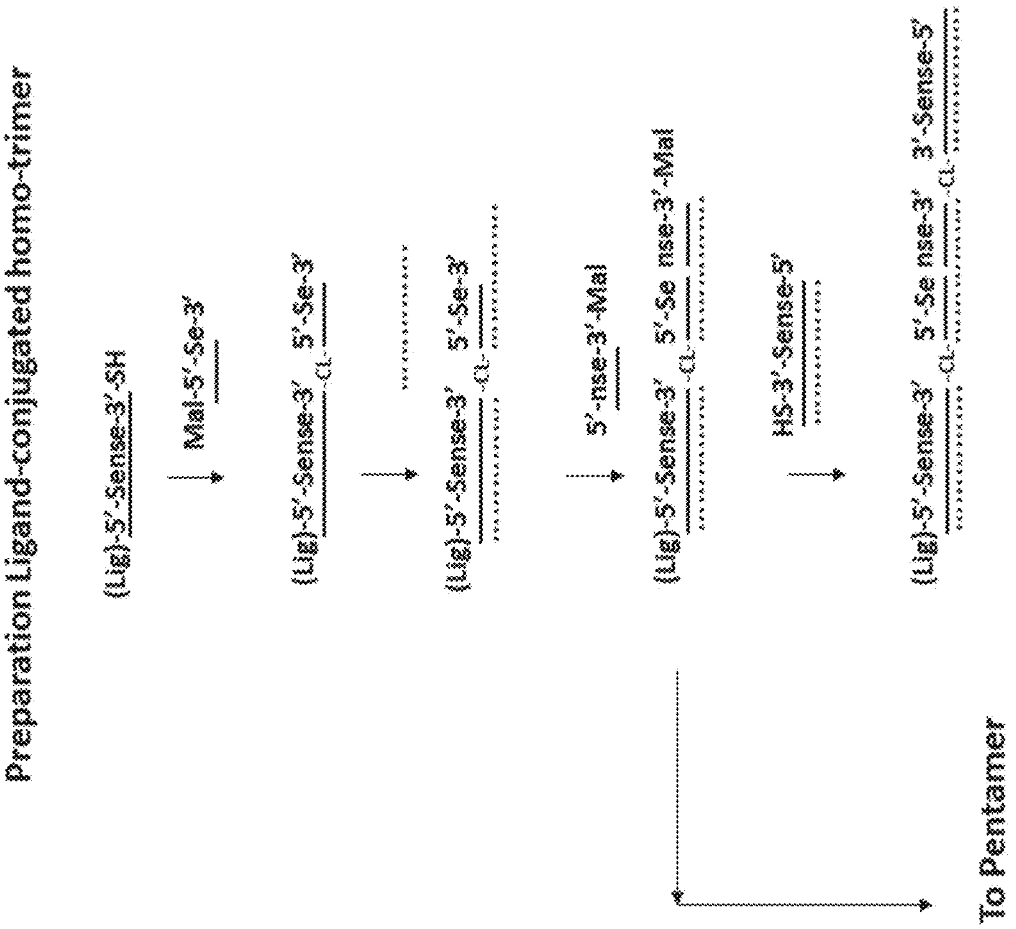
FIG. 4 illustrates a scheme for synthesizing a trimer of double-stranded oligonucleotide subunits, wherein the middle subunit comprises a split sense strand. The symbol —SH represents a thiol group; and -Mal represents a maleimide group. (Lig) represents a cell- or tissue-targeting ligand, which may be present or absent. The symbol —CL- represents a cleavable linker. "To Pentamer" means that the indicated synthetic intermediate may be isolated and used in the synthesis of a pentamer of double-stranded oligonucleotide subunits as illustrated in FIG. 6.

Example 7: Synthesis of Split-Strand Multimeric Oligonucleotides Via Annealing to One Divided Sense Strand A homo-trimer of siRNA is synthesized according to the methodology illustrated in FIG. 2. A partial sequence of an siRNA sense strand (5'-Se-3') is prepared linked via a disulfide linker (represented as —S—S— in FIG. 3) to a full-length siRNA sense strand (5'-Sense-3') on the synthesizer. A second sequence wherein the remainder of the siRNA sense sequence (5'-nse-3') is linked via a disulfide linker to a full-length siRNA strand is also synthesized. Optionally a ligand is attached to the terminus of one or both of the full-length sense strands. The two partial dimers are then annealed with three equivalents of a complementary antisense strand under the conditions described in Example 5 to form the target homo-trimeric siRNA.

Example 8: Synthesis of Split-Strand Multimeric Oligonucleotides Via Annealing to Two Divided Sense Strands A homo-tetramer of siRNA is synthesized according to the methodology illustrated in FIG. 3. A partial sequence of an siRNA sense strand (5'-Se-3') is prepared linked via a disulfide linker (represented as —S—S— in FIG. 3) to a full length siRNA sense strand on the synthesizer to yield the compound 5'-Sense-3'-S—S-5' Se-3'. Optionally, a ligand is attached to the terminus of the full length sequence. Separately, an oligomer corresponding to the remainder of the siRNA sequence and bearing a protected thiol at one terminus (5'-nse-3'-SSR) is prepared on the synthesizer. After purification the thiol is deprotected under the conditions described in Example 2 and a homo-dimer of the partial siRNA (5'-nse-3'S—CL-S3'-esn-5') is prepared via a DTME derivative (5'-nse-3'-Mal) as described in Examples 3 and 4. One equivalent of the 5'-nse-3'-homodimer (5'-nse-3'S—CL-S3'-esn-5') and two equivalents of the compound 5'-Sense-3'S—S5' Se-3' (optionally with or without a ligand) are annealed to 4 equivalents of the antisense strand under the conditions described in Example 5 to yield the desired homo-tetrameric siRNA containing three cleavable linkages.

Example 9: Synthesis of Split-Strand Multimeric Oligonucleotides Via Sequential Thiol-Maleimide Reaction and Assymetric Annealing Preparation of Building Blocks Homo-multimers (trimer to octamer) of siRNA are synthesized using the building blocks illustrated in FIG. 1 according to the methodologies described in FIGS. 1 and 4-9.

A full length siRNA sense strand with a 5' amino group and a 3' disulfide ($NH_2$-5'-Sense-3'-SSR) is prepared on the synthesizer and, as illustrated in FIG. 1, after unblocking and purification a ligand of choice is attached to a portion of the product via the amino function. The disulfide is converted to the corresponding thiol derivative as illustrated in FIG. 1 by the procedures described in Example 2.

Separately, a partial sequence of an siRNA strand corresponding to the 5'-region of the full-length strand (5'-Se-3') is prepared on the synthesizer with a disulfide at the 5'-end (RSS-5'-Se-3') which is converted to the corresponding thiol as illustrated in FIG. 1 via the procedures described in Example 2. Part of the thiolated product is further converted to the corresponding 5'-mono-DTME derivative (Mal-5'-Se-3') as illustrated in FIG. 1 by the procedures described in Example 3.

In parallel, a partial sequence of the siRNA strand corresponding to the 3'-region of the full-length strand (5'-nse-3') is prepared on the synthesizer with a disulfide at the 3'-end (5'-nse-3'-SSR)) which is converted to the corresponding thiol as illustrated in FIG. 1 via the procedures described in Example 2. Part of the thiolated product is further converted to the corresponding 3'-mono-DTME derivative (5'-nse-3'-Mal) as illustrated in FIG. 1 via the procedures described in Example 3.

In parallel, a full length siRNA antisense strand is prepared on the synthesizer, and is unblocked and purified.

Example 10: Synthesis of Split-Strand Homo-Trimer Via Sequential Thiol-Maleimide Reaction and Assymetric Annealing A homo-trimer of siRNA is prepared according to the scheme illustrated in FIG. 4 by reaction of a thiolated full-length sense strand with a partial siRNA sequence maleimide derivative Mal-5'-Se-3' via the procedures of Example 3, followed by annealing with two equivalents of the antisense strand (................). Annealing of the product with one equivalent of the partial siRNA sequence maleimide derivative 5'-nse-3'-Mal followed by reaction with one equivalent of full-length double-stranded thiolated siRNA yields the desired homo-trimer.

Figure 5:
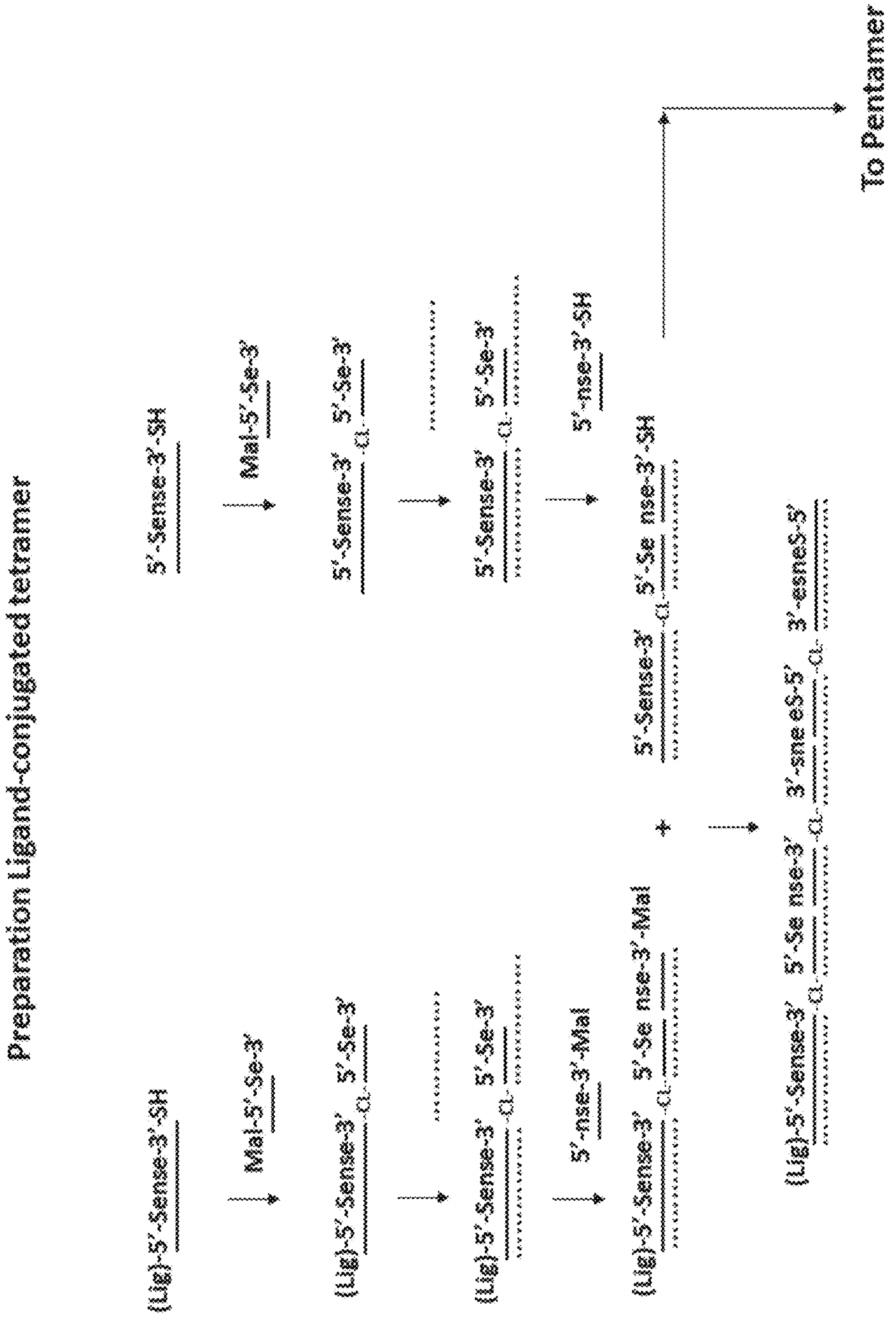
FIG. 5 illustrates a scheme for synthesizing a tetramer of double-stranded oligonucleotide subunits, wherein the middle two subunits each comprises a split sense strand. The symbol —SH represents a thiol group; and -Mal represents a maleimide group. (Lig) represents a cell- or tissue-targeting ligand, which may be present or absent. The symbol —CL- represents a cleavable linker. "To Pentamer" means that the indicated synthetic intermediate may be isolated and used in the synthesis of a pentamer of double-stranded oligonucleotide subunits as illustrated in FIG. 6.
Figure 6:
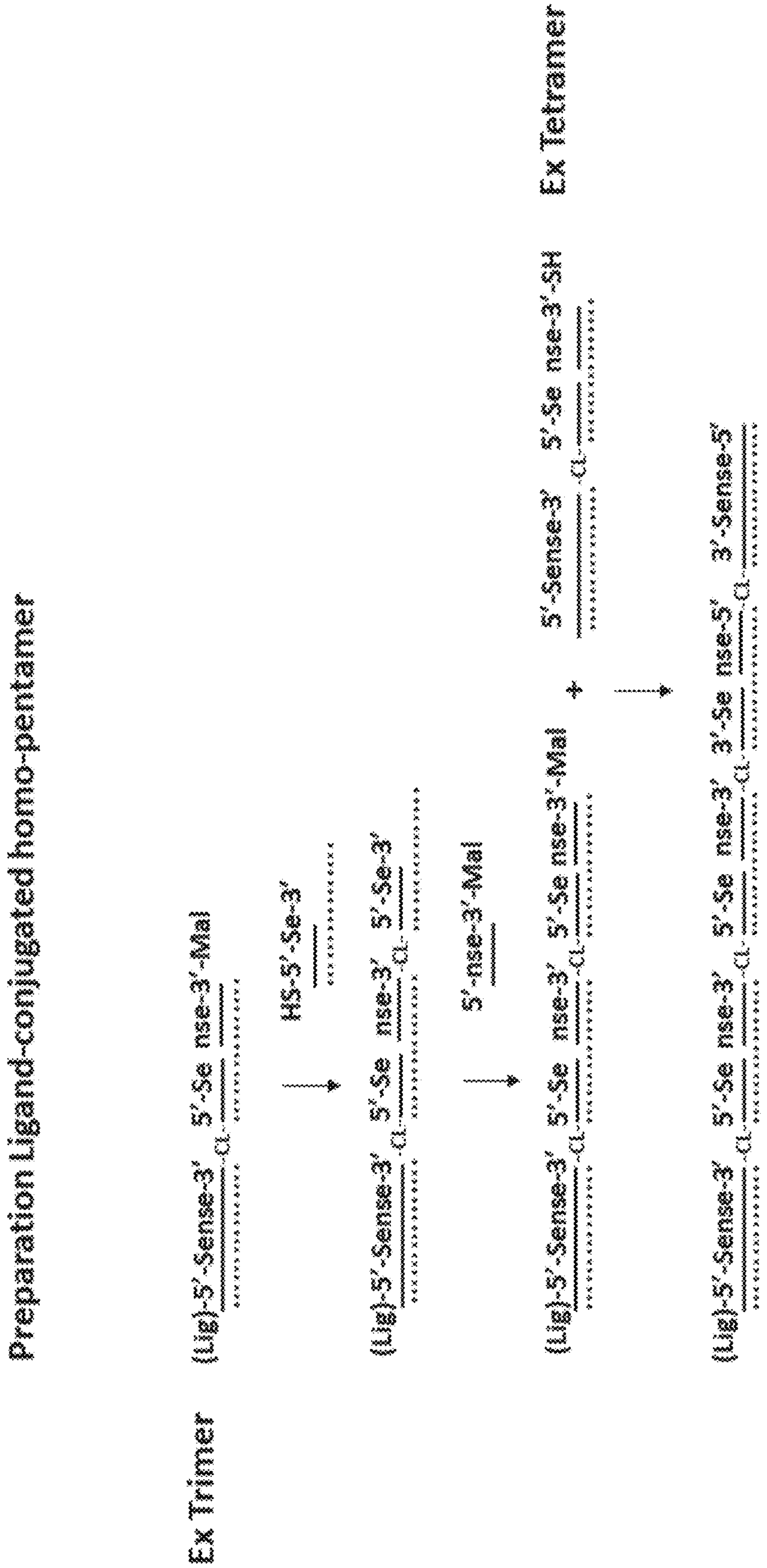
FIG. 6 illustrates a scheme for synthesizing a pentamer of double-stranded oligonucleotide subunits, wherein the middle three subunits each comprises a split sense strand. The symbol —SH represents a thiol group; and -Mal represents a maleimide group. (Lig) represents a cell- or tissue-targeting ligand, which may be present or absent. The symbol —CL- represents a cleavable linker. "Ex Trimer" means that the indicated starting material comes out of the synthesis scheme illustrated in FIG. 4. "Ex Tetramer" means that the indicated synthetic intermediate comes out of the synthesis scheme illustrated in FIG. 5.

Example 11: Synthesis of Split-Strand Homo-Tetramer Via Sequential Thiol-Maleimide Reaction and Assymetric Annealing A homo-tetramer of siRNA is prepared according to the scheme described in FIG. 5. A dimer of full-length and split-strand siRNA with a terminal maleimide is prepared as in Example 10. Separately, a second dimer of full-length and split strand siRNA with a terminal thiol is prepared as illustrated in FIG. 5 by reaction of a thiolated siRNA sense strand and a split-strand maleimide derivative Mal-5'-Se-3', followed by sequential annealing with 2 equivalents of antisense strand ............... and one equivalent of thiolated split-strand 5'-nse-3'-SH. Reaction of the maleimide-functionalized double-stranded full-length/split-strand dimer with the thiol-functionalized double-stranded full-length/split-strand dimer yields the desired homo-tetramer with 3 cleavable disulfide linkages.

Example 12: Synthesis of Split-Strand Homo-Pentamer Via Sequential Thiol-Maleimide Reactions A homo-pentamer of siRNA is prepared according to the scheme illustrated in FIG. 6. The dimer of full-length and split-strand siRNA with a terminal maleimide prepared in Example 10 is extended via sequential addition of HS-5'-Se-3' annealed to antisense strand (................), followed by 5'-nse-3'-Mal under the conditions described in Example 5 to yield the intermediate full-length/split-strand/split-strand trimer maleimide derivative. Reaction of this material with the full-length/split-strand thiol dimer prepared in Example 11 under the conditions described in Example 4 yields the desired homo-pentamer.

Figure 7:
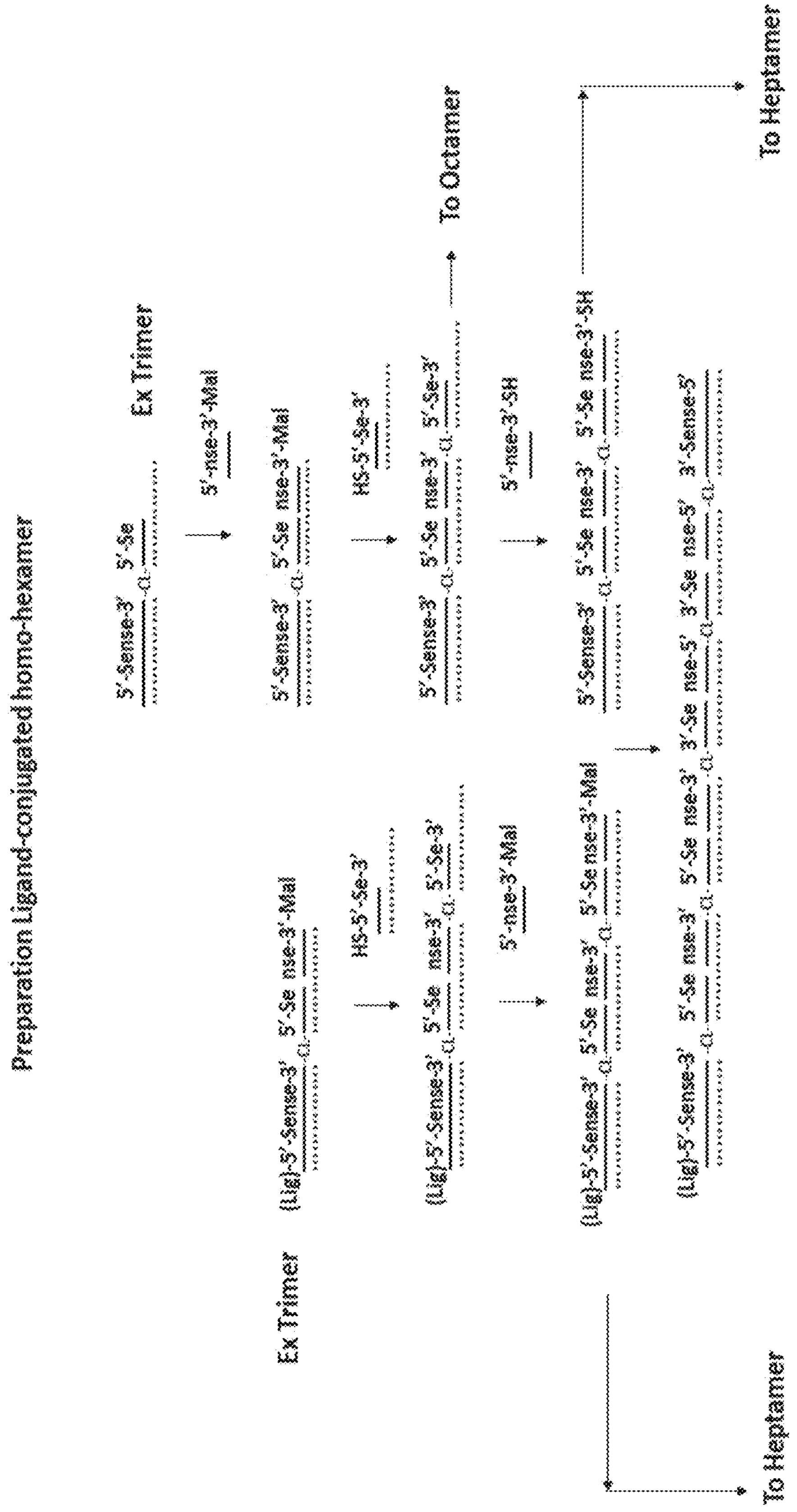
FIG. 7 illustrates a scheme for synthesizing a hexamer of double-stranded oligonucleotide subunits, wherein the middle four subunits each comprises a split sense strand. The symbol —SH represents a thiol group; and -Mal represents a maleimide group. (Lig) represents a cell- or tissue-targeting ligand, which may be present or absent. The symbol —CL- represents a cleavable linker. "To Heptamer" means that the indicated synthetic intermediate may be isolated and used in the synthesis of a heptamer of double-stranded oligonucleotide subunits as illustrated in FIG. 8. "To Octamer" means that the indicated synthetic intermediate may be isolated and used in the synthesis of an octamer of double-stranded oligonucleotide subunits as illustrated in FIG. 9.
Figure 8:
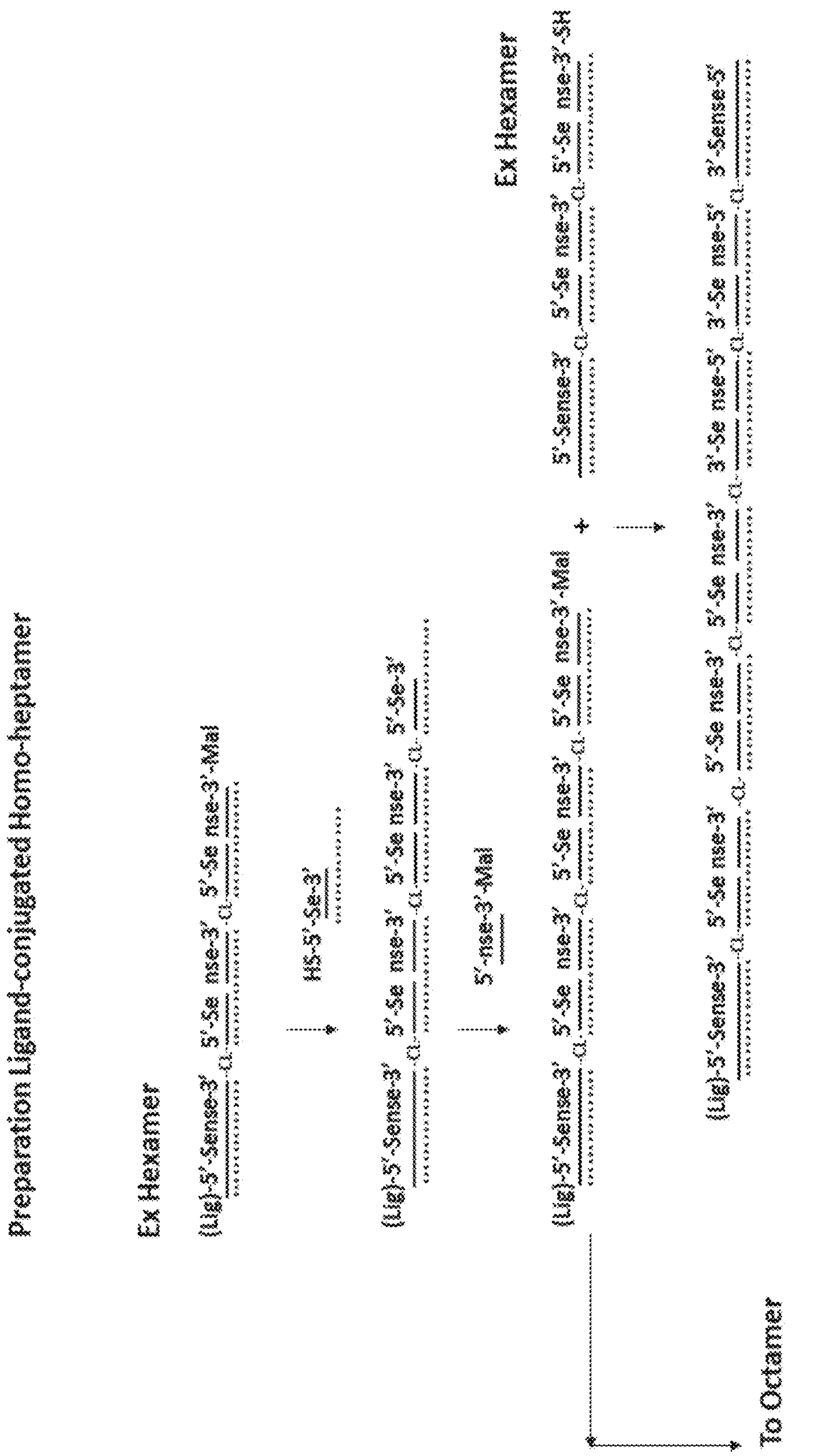
FIG. 8 illustrates a scheme for synthesizing a heptamer of double-stranded oligonucleotide subunits, wherein the middle five subunits each comprises a split sense strand. The symbol —SH represents a thiol group; and -Mal represents a maleimide group. (Lig) represents a cell- or tissue-targeting ligand, which may be present or absent. The symbol —CL- represents a cleavable linker. "Ex Hexamer" means that the indicated starting material or synthetic intermediate comes out of the synthesis scheme illustrated in FIG. 7. "To Octamer" means that the indicated synthetic intermediate may be isolated and used in the synthesis of an octamer of double-stranded oligonucleotide subunits as illustrated in FIG. 9.
Figure 9:
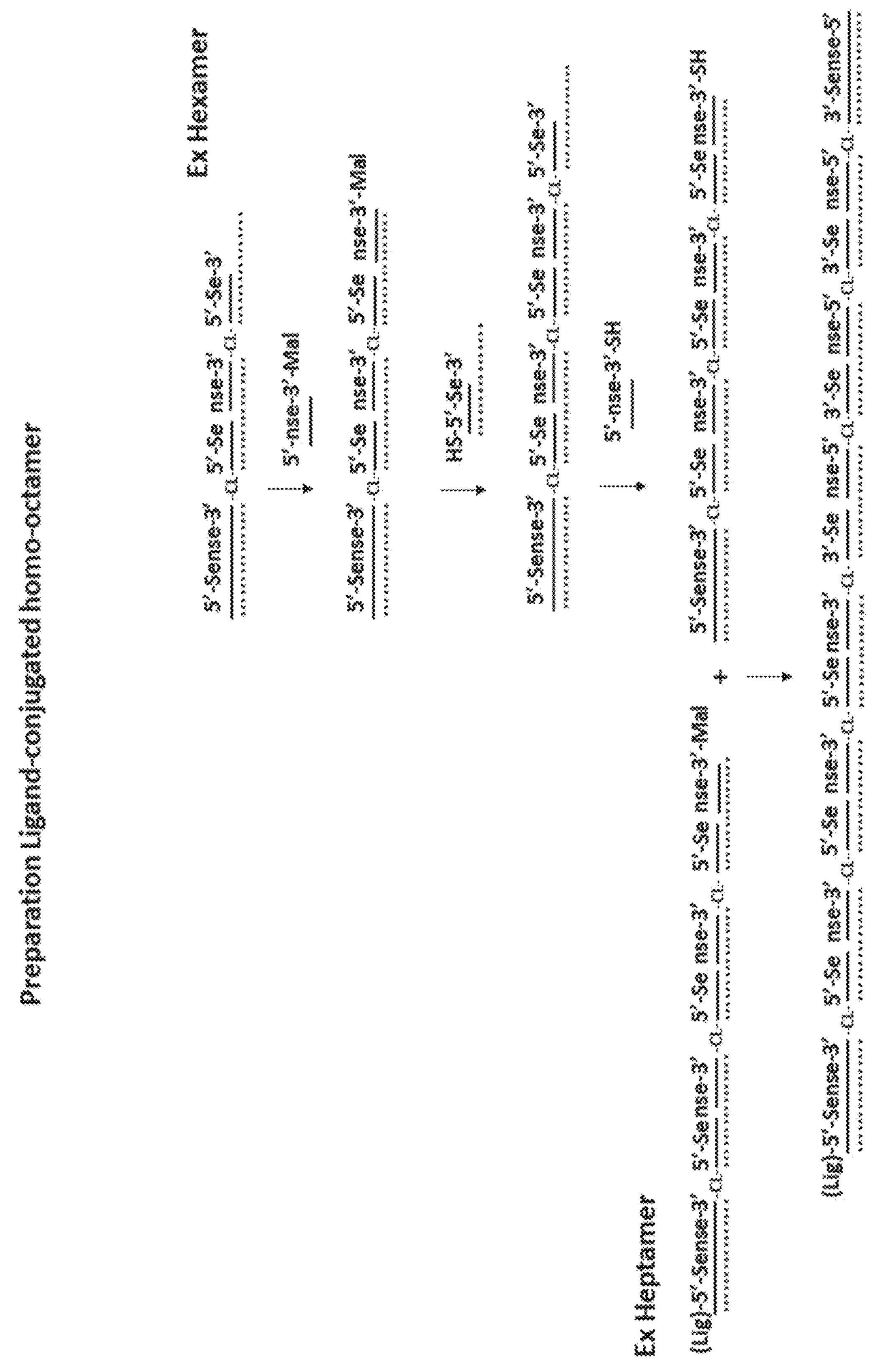
FIG. 9 illustrates a scheme for synthesizing an octamer of double-stranded oligonucleotide subunits, wherein the middle six subunits each comprises a split sense strand. The symbol —SH represents a thiol group; and -Mal represents a maleimide group. (Lig) represents a cell- or tissue-targeting ligand, which may be present or absent. The symbol —CL- represents a cleavable linker. "Ex Hexamer" means that the indicated starting material comes out of the synthesis scheme illustrated in FIG. 7. "Ex Heptamer" means that the indicated synthetic intermediate comes out of the synthesis scheme illustrated in FIG. 8.

Example 13: Synthesis of Split-Strand Homo-Hexamer Via Sequential Thiol-Maleimide Reactions A homo-hexamer of siRNA is prepared according to the scheme illustrated in FIG. 7 of chain extension of the intermediates prepared in Example 10 by sequential additions of 5'-nse-3'-Mal, HS-5'-Se-3' annealed to antisense strand (...............), and 5'-nse-3'-SH, as illustrated in FIG. 7 under the conditions described in Example 5 The two trimer chains are then linked by a thiol/maleimide reaction under conditions described in Example 4.

Example 14: Synthesis of Split-Strand Homo-Heptamer Via Sequential Thiol-Maleimide Reactions A homo-heptamer of siRNA is prepared according to the scheme illustrated in FIG. 8 by chain extension of the maleimide-derivatized trimer prepared in Example 13 through sequential additions of HS-5'-Se-3' annealed to antisense strand (...............) and 5'-nse-3'-Mal and 5'-nse-3'-SH under the conditions described in Example 5, followed by linking of the resulting maleimide-derivatized tetramer with the thiol-derivatized trimer from Example 13 by thiol/maleimide reaction under conditions described in Example 4.

Example 15: Synthesis of Split-Strand Homo-Octamer Via Sequential Thiol-Maleimide Reactions A homo-octamer of siRNA is prepared according to the scheme illustrated in FIG. 9 by chain extension of the partial trimer intermediate from Example 13 through sequential additions of 5'-nse-3'-Mal, HS-5'-Se-3' annealed to antisense strand (................), and 5'-nse-3'-SH under the conditions described in Example 5. The resulting thiolated tetramer is then linked to the maleimide-functionalized tetramer obtained in Example 14 by reaction of the thiol and maleimide moieties under conditions described in Example 4.

Figure 11:
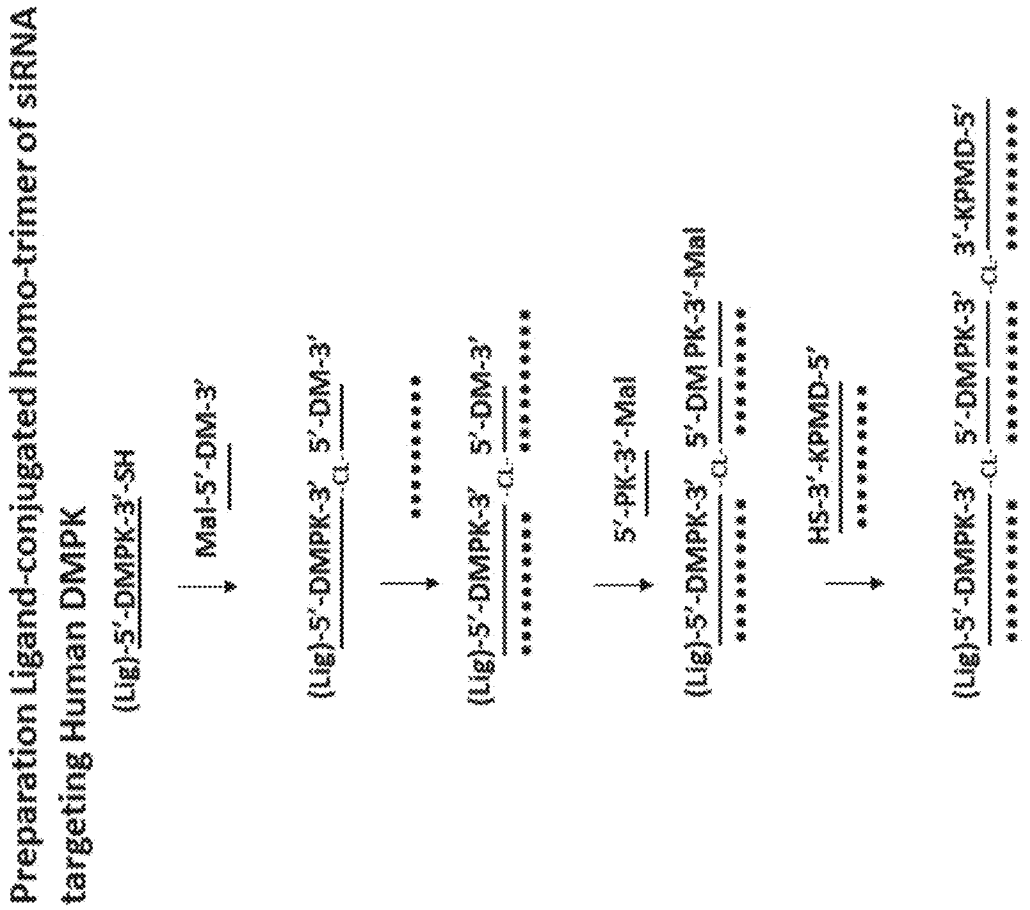
FIG. 11 illustrates a scheme for synthesizing a trimer of siRNA targeting human DMPK mRNA. The symbol —SH represents a thiol group; and -Mal represents a maleimide group. (Lig) represents a cell- or tissue-targeting ligand, which may be present or absent. The symbol —CL- represents a cleavable linker.

Example 16: Synthesis of Split-Strand Homo-Trimer of siDMPK Via Sequential Thiol-Maleimide Reaction and Assymetric Annealing A homo-trimer of siRNA targeting Myotonic Dystrophy Protein Kinase mRNA (DMPK) is prepared according to the Scheme in FIG. 11. A full length DMPK sense strand is prepared on the synthesizer with a 3'-thiol residue using the methods described in Example 2. A partial sequence of the DMPK sense strand (5'-DM-3') with a 5'-thiol (HS-5'-DM-3') is also prepared on the synthesizer and converted the corresponding mono-DTME derivative (Mal-5'-DM-3') by the methods described in Examples 2 and 3. The thiolated full-length strand and the DTME-derivatized partial-length DMPK strand are then reacted together to form the corresponding single-stranded partial dimer which is then annealed with two equivalents of full-length DMPK antisense strand (...............) according to the conditions in Example 5.

A second sequence comprising the remainder of the siRNA sense sequence (5'-PK-3') derivatized with a 3'-thiol (5'-PK-3'-SH) is also synthesized, converted to the corresponding mono-DTME derivative according the the procedures in Example 3 and annealed with the double-stranded partial dimer to yield the double-stranded full-length/split-strand dimer of DMPK with a 3'terminal maleimide group. This material is then reacted with 3'-thiolated double-stranded full-length DMPK siRNA to form the desired homotrimer of DMPK siRNA.

Figure 12:
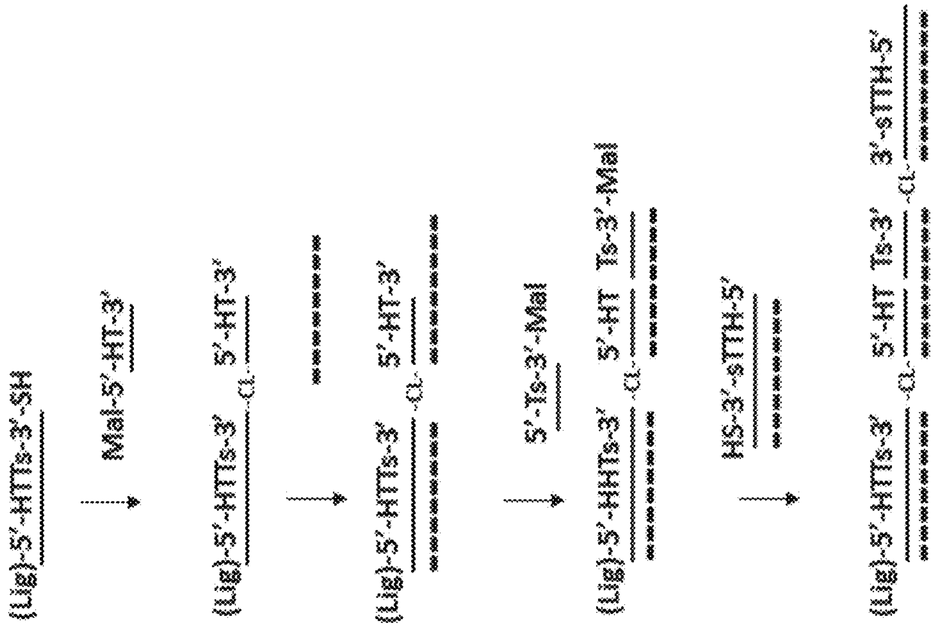
FIG. 12 illustrates a scheme for synthesizing a trimer of siRNA targeting human Huntingtin mRNA. The symbol —SH represents a thiol group; and -Mal represents a maleimide group. (Lig) represents a cell- or tissue-targeting ligand, which may be present or absent. The symbol —CL- represents a cleavable linker.

Example 17: Synthesis of Split-Strand Homo-Trimer of siHTT Via Sequential Thiol-Maleimide Reaction and Assymetric Annealing A homo-trimer of siRNA targeting Huntingtin mRNA (HTT) is prepared according to the Scheme illustrated in FIG. 12. A full-length HTT sense strand (HTTs) is prepared on the synthesizer with a 3'-thiol residue using the methods described in Example 2. A partial sequence of the HTT sense strand (5'-HT-3') with a 5'-thiol (HS-5'-HT-3') is also prepared on the synthesizer and converted the corresponding mono-DTME derivative (Mal-5'-HT-3') by the methods described in Examples 2 and 3. The thiolated full length (HTTs) strand and the DTME partial-length (HT) strand are then reacted together to form the corresponding single-stranded partial dimer which is then annealed with two equivalents of full-length HTTs antisense strand (................) according to the conditions in Example 5.

A second sequence wherein the remainder of the siRNA sense sequence (5'-Ts-3') derivatized with a 3'-thiol (5'-Ts-3'-SH) is also synthesized, converted to the corresponding mono-DTME derivative according the the procedures in Example 3 and annealed with the double-stranded partial dimer to yield the double-stranded full-length/split-strand dimer of HTT with a 3'-terminal maleimide group. This material is then reacted with 3'-thiolated double-stranded full-length HTT siRNA to form the desired homotrimer of HTT siRNA.

Figure 10:
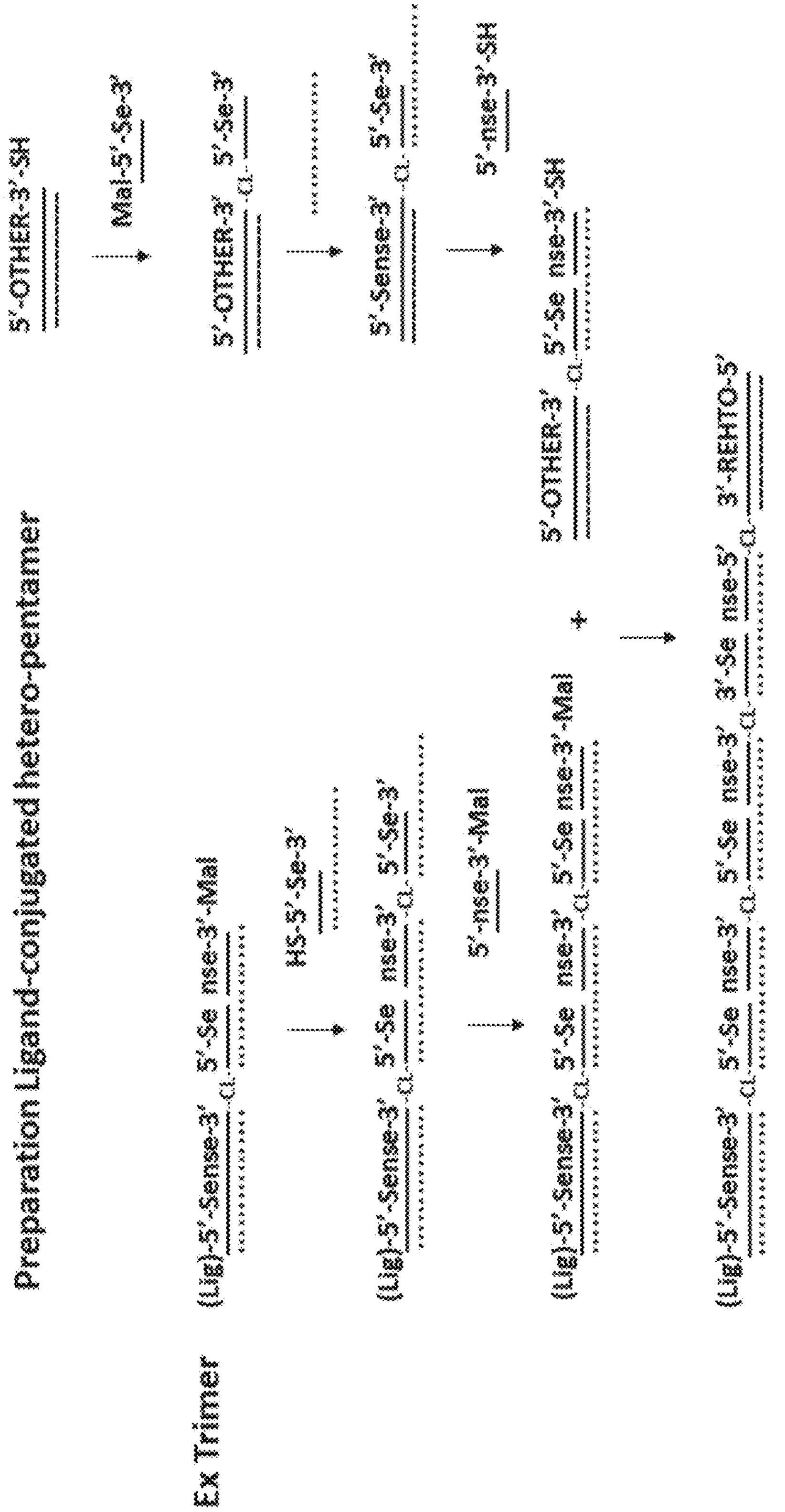
FIG. 10 illustrates a scheme for synthesizing hetero-pentamer of double-stranded oligonucleotide subunits, wherein the middle three subunits each comprises a split sense strand. The hetero-pentamer comprises 4 subunits of a first oligonucleotide; one of which comprises an intact sense strand (designated as 5'-Sense-3') and the other three of which each comprise a split sense strand comprised of two partial strands designated as 5'-Se and nse-3'. 5'-OTHER-3' represents an oligonucleotide sequence that is different from 5'-Sense-3'. As will be readily understood, the complementary strand for 5'-OTHER-3' is different from the complementary strand for 5'-Sense-3'. The symbol —SH represents a thiol group; and -Mal represents a maleimide group. (Lig) represents a cell- or tissue-targeting ligand, which may be present or absent. The symbol —CL- represents a cleavable linker. "Ex Trimer" means that the indicated starting material comes out of the synthesis scheme illustrated in FIG. 4.

Example 18: Synthesis of Split-Strand Hetero-Pentamer Via Sequential Thiol-Maleimide Reactions A hetero-pentamer of siRNA is prepared according to the scheme illustrated in FIG. 10. The dimer of a first siRNA having a intact subunit and a split-strand subunit with a terminal maleimide (as prepared in Example 10) is extended via sequential additions of HS-5'-Se-3' annealed to antisense strand (................), followed by 5'-nse-3'-Mal under the conditions described in Example 5 to yield the intermediate intact/split-strand/split-strand trimer maleimide derivative.

Separately, an intact double-stranded second siRNA (having a sequence different from the first siRNA) with a 3'-thiol is reacted with a 5'-maleimido derivative of the 5'-partial sequence of the sense strand of the first siRNA (Mal-5'-Se-3') and the product sequentially annealed with the full-length antisense strand (................) of the first siRNA, followed by a 3'-thiolated derivative of the 3'-partial sequence of the sense strand of the first siRNA (5'-nse-3'-SH) to yield the thiolated hetero-dimer intermediate.

Reaction of the thiolated hetero-dimer intermediate with the homo-trimer maleimide derivative yields the desired hetero-pentamer having four subunits of the first siRNA and one subunit of the second siRNA.

What is claimed is:

1. A multimeric oligonucleotide comprising Structure 6:

(Structure 6)

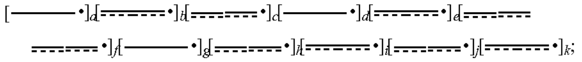

wherein:

each ——— is a single-stranded oligonucleotide, wherein each single-stranded oligonucleotide is 10-28 nucleotides in length;

each — is a partial single-stranded oligonucleotide, wherein each partial single-stranded oligonucleotide is 5-14 nucleotides in length;

each • is a covalent linker;

each .............. is a complementary strand; and each of a, b, c, d, e, f, g, h, i, j, and k is independently an integer greater than or equal to zero, with the proviso that at least one of c, e, h, and j is greater than or equal to 1.

2. The multimeric oligonucleotide of claim 1, wherein the multimeric oligonucleotide comprises Structure 7:

(Structure 7)

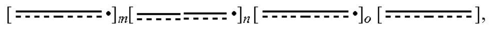

wherein:

m and n are each independently an integer greater than or equal to 1; and o is an integer greater than or equal to 0.

3. The multimeric oligonucleotide of claim 2, wherein the multimeric oligonucleotide comprises one of the following structures:

(Structure 10)

(Structure 11)

(Structure 12)

(Structure 13)

(Structure 14)

and (Structure 15)

4. The multimeric oligonucleotide of claim 1, wherein each subunit in the multimeric oligonucleotide is RNA, DNA, or an artificial or non-natural nucleic acid analog.

5. The multimeric oligonucleotide of claim 1, wherein at least one subunit is a single-stranded subunit.

6. The multimeric oligonucleotide of claim 5, wherein the at least one single-stranded subunit is an antisense oligonucleotide.

7. The multimeric oligonucleotide of claim 1, wherein at least one covalent linker • is a cleavable covalent linker.

8. The multimeric oligonucleotide of claim 7, wherein the cleavable covalent linker comprises an acid cleavable bond, a reductant cleavable bond, a bio-cleavable bond, or an enzyme cleavable bond.

9. The multimeric oligonucleotide of claim 1, wherein each covalent linker • is the same.

10. The multimeric oligonucleotide of claim 1, wherein at least one covalent linker • is different from the other covalent linkers.

11. The multimeric oligonucleotide of claim 1, at least two subunits are joined by a covalent linker • between the 3' end of a first subunit and the 3' of a second subunit.

12. The multimeric oligonucleotide of claim 1, wherein at least two subunits are joined by a covalent linker • between the 5' end of a first subunit and the 5' of a second subunit.

13. A composition comprising the multimeric oligonucleotide of claim 1 and a pharmaceutically acceptable excipient.

14. The multimeric oligonucleotide of claim 1, wherein the single-stranded oligonucleotide is a RNA.

* * * * *

SEQUENCE LISTING

```
Sequence total quantity: 10
SEQ ID NO: 1            moltype =   length =
SEQUENCE: 1
000

SEQ ID NO: 2            moltype =   length =
SEQUENCE: 2
000

SEQ ID NO: 3            moltype =   length =
SEQUENCE: 3
000

SEQ ID NO: 4            moltype = AA  length = 5
FEATURE                 Location/Qualifiers
REGION                  1..5
                        note = Synthetic
source                  1..5
                        mol_type = protein
                        organism = synthetic construct
SEQUENCE: 4
APRPG                                                   5

SEQ ID NO: 5            moltype = AA  length = 13
FEATURE                 Location/Qualifiers
REGION                  1..13
                        note = Synthetic
source                  1..13
                        mol_type = protein
                        organism = synthetic construct
SEQUENCE: 5
CNGRCVSGCA GRC                                          13

SEQ ID NO: 6            moltype = AA  length = 31
FEATURE                 Location/Qualifiers
REGION                  1..31
```

-continued

```
                       note = Synthetic
source                 1..31
                       mol_type = protein
                       organism = synthetic construct
SEQUENCE: 6
KDEPQRRSAR LSAKPAPPKP EPKPKKAPAK K                                  31

SEQ ID NO: 7           moltype = AA  length = 5
FEATURE                Location/Qualifiers
REGION                 1..5
                       note = Synthetic
source                 1..5
                       mol_type = protein
                       organism = synthetic construct
SEQUENCE: 7
CGKRK                                                               5

SEQ ID NO: 8           moltype = AA  length = 9
FEATURE                Location/Qualifiers
REGION                 1..9
                       note = Synthetic
source                 1..9
                       mol_type = protein
                       organism = synthetic construct
SEQUENCE: 8
CRGDKGPDC                                                           9

SEQ ID NO: 9           moltype =   length =
SEQUENCE: 9
000

SEQ ID NO: 10          moltype =   length =
SEQUENCE: 10
000
```